United States Patent
Falzarano et al.

(10) Patent No.: US 12,061,150 B2
(45) Date of Patent: Aug. 13, 2024

(54) DETECTION OF BIOLOGICAL SUBSTANCES

(71) Applicant: ORB XYZ, INC., San Francisco, CA (US)

(72) Inventors: Lorenzo Falzarano, San Francisco, CA (US); Andreia Michelle Smith-Moritz, Oakland, CA (US)

(73) Assignee: ORB XYZ, INC., Berkeley, CA (US)

( * ) Notice: Subject to any disclaimer, the term of this patent is extended or adjusted under 35 U.S.C. 154(b) by 762 days.

(21) Appl. No.: 17/059,690

(22) PCT Filed: May 31, 2019

(86) PCT No.: PCT/US2019/035016
§ 371 (c)(1),
(2) Date: Nov. 30, 2020

(87) PCT Pub. No.: WO2019/232450
PCT Pub. Date: Dec. 5, 2019

(65) Prior Publication Data
US 2021/0199588 A1   Jul. 1, 2021

Related U.S. Application Data

(60) Provisional application No. 62/679,603, filed on Jun. 1, 2018.

(51) Int. Cl.
*B01L 3/00* (2006.01)
*B01F 23/00* (2022.01)
(Continued)

(52) U.S. Cl.
CPC .......... *G01N 21/6486* (2013.01); *C12Q 1/04* (2013.01); *G01N 33/1826* (2013.01)

(58) Field of Classification Search
CPC .......... G01N 21/6486; G01N 33/1826; G01N 21/8507; G01N 21/94; G01N 2201/0221; C12Q 1/04
See application file for complete search history.

(56) References Cited

U.S. PATENT DOCUMENTS 5,262,841 A * 11/1993 Blesener ............... G01N 21/53
356/336
9,442,070 B1    9/2016 Hug et al.
(Continued)

FOREIGN PATENT DOCUMENTS

WO    2015/130792 A1    9/2015

OTHER PUBLICATIONS

Agresti, 1996, An Introduction to Categorical Data Analysis, John Wiley & Sons, Inc., New York, Chapter 8, pp. 244-266.
(Continued)

*Primary Examiner* — Jennifer Wecker
*Assistant Examiner* — Oyeleye Alexander Alabi
(74) *Attorney, Agent, or Firm* — Brown Rudnick LLP; Adam M. Schoen

(57) ABSTRACT

The invention generally relates to detecting biological substances. In certain aspects, the invention is directed to a method directing one or more wavelengths of light within a deep ultraviolet (UV) spectrum into a medium to excite a biological substance in the medium, detect emission from the excited biological substance via a plurality of semiconductor photodetectors, and analyze the deep UV emission data for presence of a deep UV spectral signature indicative of the biological substance, wherein presence of the deep UV spectral signature indicates that the medium comprises a biological substance. The invention is also directed to identifying a pathogen in a medium comprising a pathogen and a non-pathogen biological substance.

18 Claims, 37 Drawing Sheets

(51) Int. Cl.
*B01F 23/41* (2022.01)
*B01F 101/23* (2022.01)
*B23Q 17/24* (2006.01)
*C12M 1/34* (2006.01)
*C12Q 1/04* (2006.01)
*C12Q 1/18* (2006.01)
*G01N 21/3577* (2014.01)
*G01N 21/359* (2014.01)
*G01N 21/39* (2006.01)
*G01N 21/45* (2006.01)
*G01N 21/64* (2006.01)
*G01N 30/12* (2006.01)
*G01N 30/68* (2006.01)
*G01N 30/70* (2006.01)
*G01N 30/72* (2006.01)
*G01N 30/88* (2006.01)
*G01N 33/00* (2006.01)
*G01N 33/18* (2006.01)
*G01N 33/50* (2006.01)
*G01N 33/68* (2006.01)

(56) References Cited

U.S. PATENT DOCUMENTS

| | | |
|---|---|---|
| 2003/0128737 A1 | 7/2003 | McGrath et al. |
| 2004/0043443 A1* | 3/2004 | Lejeune ............... G01N 1/2273 |
| | | 435/297.2 |
| 2008/0030712 A1 | 2/2008 | Tokhtuev et al. |
| 2008/0179541 A1* | 7/2008 | LeBoeuf ............ G01N 21/6486 |
| | | 250/459.1 |
| 2009/0075843 A1* | 3/2009 | Jiang ..................... C40B 60/12 |
| | | 506/39 |
| 2011/0050431 A1 | 3/2011 | Hood et al. |
| 2013/0153777 A1 | 6/2013 | Sexton et al. |
| 2013/0200276 A1 | 8/2013 | Poteet et al. |
| 2015/0168288 A1* | 6/2015 | Binnie ............... G01N 15/1434 |
| | | 250/461.1 |
| 2016/0033407 A1 | 2/2016 | Tokhtuev et al. |
| 2016/0084707 A1 | 3/2016 | Scott et al. |
| 2017/0038301 A1 | 2/2017 | Flanagan et al. |
| 2018/0042511 A1 | 2/2018 | Atanackovic |
| 2019/0056304 A1* | 2/2019 | Gershtein ......... B01L 3/502715 |

OTHER PUBLICATIONS

Duda, 2001, Pattern Classification, Second Edition, John Wiley & Sons, Inc., 39 pages.

Yli-Huumo, 2016, Where Is Current Research on Blockchain Technology?—A Systematic Review, PLOS One, 27 pages.

Bhartia, 2008, Classification of Orgnic and Biological Materials with Deep Ultraviolet Excitation, Applied Spectroscopy, 62(10):1070-1077.

Extended European Search Report issued in European Application No. 19809984.8, date of mailing: Jan. 7, 2022, 12 pages.

\* cited by examiner

| TARGET |
|---|
| Biphenyl |
| B-estradiol |
| Aniline |
| Naphthalene |
| Benzimidazole |
| carbendazim |
| Dimethyl phthalate |
| carbaryl-d7 |
| Benzo a pyrene |
| Dimetyl pthalate |
| Styrene |
| Bisphenol S |
| Albumin |
| Dibutyl phthalate |
| Bisphenol S |
| chlorpyrifos |
| P-xylene |
| Ibuprofen |
| Biphenyl |
| 1napthol |
| Diisodecyllphthalate |
| Diethyl phthalate |
| testosterone |
| Atrazine |
| Imidazole |
| Clarithramycin |
| Acetaminophan |
| Toulene |
| Poly(ethylene terephthalate) |
| Phenanthrene |
| Bisphenol A |

FIG. 16

| Target | Noise added | Limits of Detection (LOD) |
|---|---|---|
| BPA | 10% | 0.0156 ppm |
| BPS | 10% | 0.0156 ppm |
| Beta-Estradiol | 10% | 0.0039 ppm |
| 17aEthrynyl estradiol | 10% | 0.00195 ppm |

BPA with 10% noise- 0.0156ppm +- 0.003ppm (at 20% error) optimized bandpass and excitation selection

```
Excitation BP1 BP2 BP3 BP4 BP5 BP6 prediction   Error%
   [1,] 246 310 328 350 366 382 400 0.01401240 19.18584
   [2,] 246 310 328 348 366 382 398 0.01555272 19.85481
   [3,] 252 308 330 348 364 380 400 0.01556496 19.17771
   [4,] 262 300 322 342 358 376 396 0.01499054 18.57263
   [5,] 262 300 322 340 360 378 398 0.01493735 18.62849
   [6,] 262 300 322 338 360 376 392 0.01601121 18.98303
   [7,] 276 300 316 336 352 370 400 0.01499285 19.82477
```

FIG. 17

| KEY: | Component |
|---|---|
| LED | OPTAN-280K-BL |
| L1 | 35 mm focal length UV fused sillica lens |
| L2 | 20 mm focal length fused sillica lens |
| L3 | 20 mm focal length fused sillica lens |
| F1 | Semrock 280 nm UV filter |
| PD | Detector |
| Fiberoptic coupler | SMA-905 free space to fiber couple |
| Incidence Angle | ~35deg |

FIG. 37
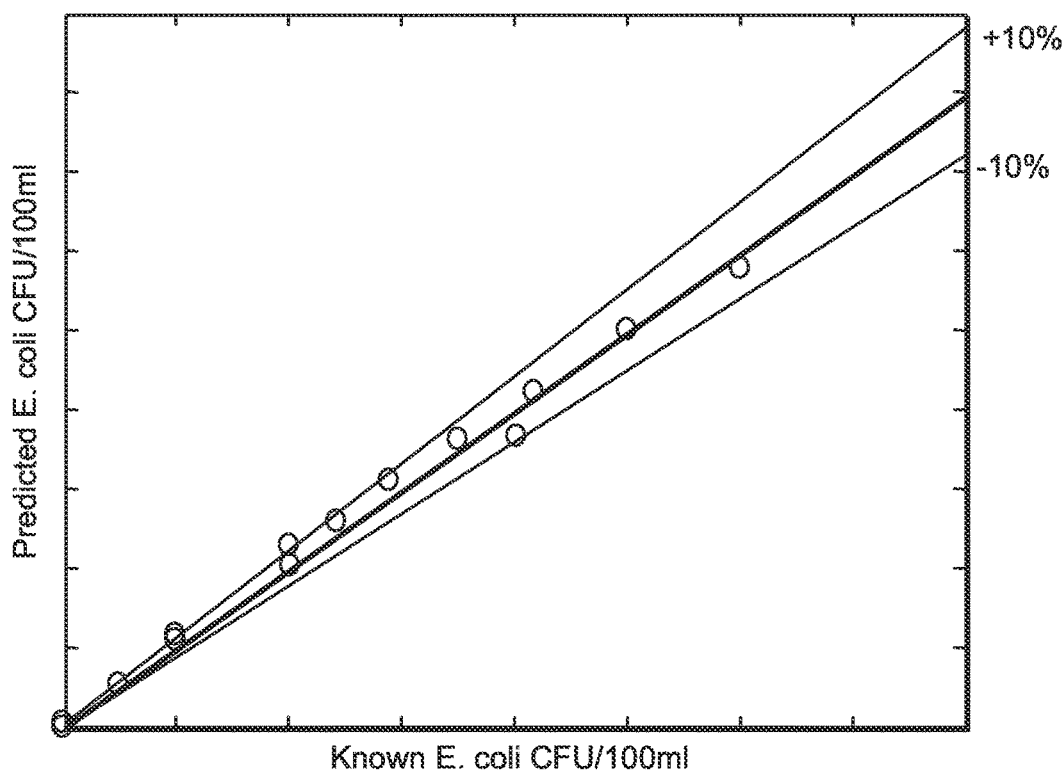
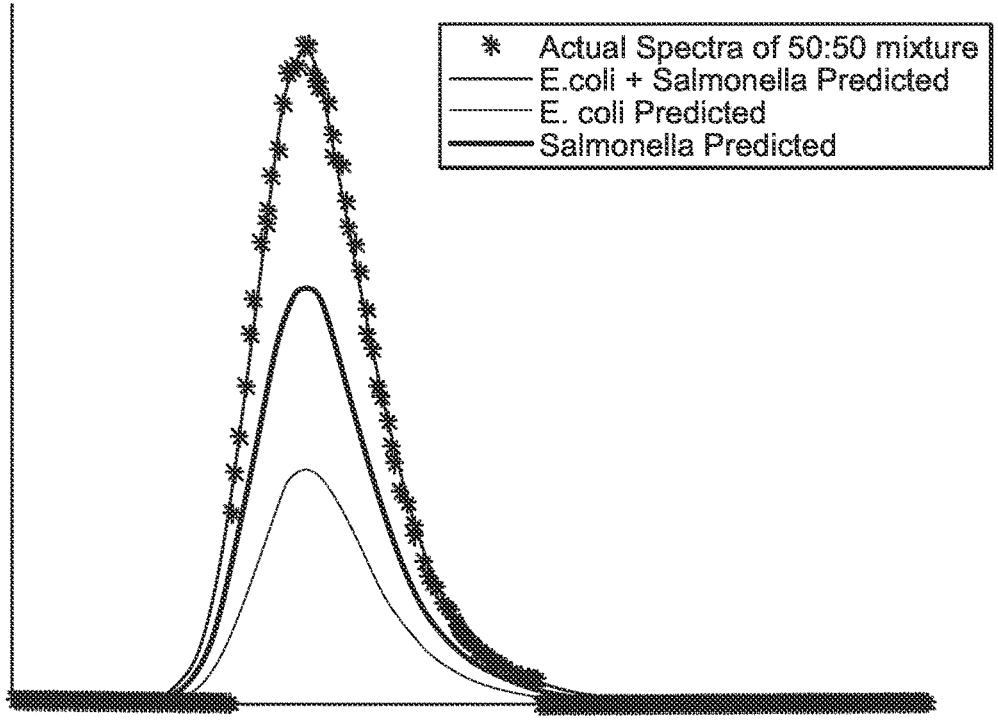
FIG. 38

$R^2$ Predicted vs Actual Composition

| | |
|---|---|
| E. coli 0157:H7 + Salmonella | 0.97 |
| E. coli 0157:H7 + Staphylococcus *aureus* | 0.99 |
| E. coli ATCC 11775 + Pseudomonas putida | 0.97 |
| Salmonella + Tyrosine, tryptophan, orange juice, and misc biological material | 0.99 |
| Salmonella + Staphylococcus *aureus* | 0.98 |
| Salmonella + Pseudomonas *putida* | 0.87 |
| Staphylococcus aureus + Pseudomonas *putida* | 0.91 |

R² Predicted vs Actual Viability

| | |
|---|---|
| Dead vs Alive: Salmonella | 0.96 |
| Dead vs Alive: E. coli DH5alpha | 0.93 |
| Dead vs Alive: Listeria *welshmeri* | 0.90 |
| Dead vs Alive Staphylococcus *aureus* | 0.80 |

| Target | Orb Detection | | "Gold Standard" Membrane Filtration Coliform Test | |
|---|---|---|---|---|
| *99% of bacteria are non-culturable* | | | | |
| E. coli O157 50 cfu/ml | | + | | + |
| Salmonella $2 \times 10^8$ cfu/ml | | + | | - |
| E. coli (Strain A) $1 \times 10^7$ cfu/ml | | + | | - |
| E. coli (Strain B) $1 \times 10^7$ cfu/ml | | + | | - |

FIG. 45

Selection of Detection Capabilities To Date

| | |
|---|---|
| E. coli 0157:H7 | Bacteria |
| E. coli - non pathogenic | Bacteria |
| Salmonella enterica | Bacteria |
| Staphylococcus *aureus* | Bacteria |
| Listeria monocytogenes | Bacteria |
| Listeria welshimeri | Bacteria |
| Listeria seeligeri | Bacteria |
| Pseudomonas | Bacteria |
| Bacillus Subtillis | Bacteria |
| 1-napthol | Pesticide |
| Acetamenophen | Pharmaceutical |
| Aniline | Industrial Chemical |
| Atrazine | Pesticide |
| B-estradiol | Hormone (estrogen) |
| Benzimidazole | Industrial Chemical |
| Benzimidazolem | Industrial Chemical |
| Benzo[a]pyrene | Industrial Chemical |
| Bisphenol A (BPA) | Industrial Chemical |
| Clarithramycin | Pharmaceutical |
| Dibutylphthalate | Industrial Chemical |
| Diisodecylphthalate | Industrial Chemical |
| Dimetyl-pthalate | Industrial Chemical |
| Ibuprofen | Pharmaceutical |
| Imidazole | Pharmaceutical |
| Napthalene | Industrial Chemical |
| P-xylene | Industrial Chemical |
| Toulene | Industrial Chemical |

FIG. 46

DETECTION OF BIOLOGICAL SUBSTANCES

CROSS-REFERENCE TO RELATED APPLICATION(S)

This application is a national stage entry of PCT/US2019/035016, filed May 31, 2019, which claims the benefit of and priority to U.S. Provisional Patent Application No. 62/679,603 filed Jun. 1, 2018, the contents of which are incorporated by reference herein in their entirety.

FIELD OF THE INVENTION

The invention generally relates to systems and methods for detecting a biological substance in a medium.

BACKGROUND

Water, food, and healthcare industries worldwide are subject to contamination. 10% of global disease burden is caused by waterborne microbiological contamination. In India alone, there are 1.4 million preventable child deaths each year from contaminated water. Further, 77 million Americans drank tap water from utilities that violated contaminant safety regulations in 2017. In the United States, 15 million homes use private wells for their drinking water with no ability to test in real time. The United States food industry reported approximately $52 billion of lost revenue yearly from product recalls and safety expenditures. Contamination is also prevalent in the healthcare industry. There are $38 billion in extra costs each year in the United States resulting from hospital-acquired infections.

Currently available pathogen testing methods are complex, expensive, and slow. The testing processes may include filtering, culturing, incubation, and staining by scientists in well-equipped laboratories. For example, contamination testing of food requires holding the food product for 24 hours to two weeks while bacteria cultures grow. Additionally, certain testing techniques damage or destroy the sample.

If results from testing are not available for a prolonged period of time (e.g., 24 hours, two weeks, or longer), a minor contamination problem may turn into a major event. Public water resources may be infected, food production lines may be contaminated, and hospital infections may spread quickly. Without early detection and reporting of testing results, the public may be subject to widespread contamination.

SUMMARY

The present invention provides a quick, affordable, easy to use method for detecting and distinguishing between biological substances, particularly pathogen in a medium, such as water. The present invention is portable and easy to use. Results are delivered within seconds. In addition to detecting whether or not a biological substance is present, the present invention identifies and also quantifies the biological substance. Importantly, the systems and methods of the invention can further differentiate the biological substance from other biological substances present in the tested sample, e.g., pathogen from other biological substances and different pathogen from each other. Consumers can rely on their own device and their own testing instead of risking consumption of contaminated food from suppliers. The invention delivers real-time biological safety monitoring of process waters and surfaces for the water, pharmaceutical, semiconductor and food and beverage industries.

Particularly, the invention takes advantage of the fact that pathogen in a medium auto-fluorescence when excited with ultraviolet light (e.g., deep ultraviolet light (deep UV)). Using the proprietary algorithms and databases of the invention, a unique deep UV signature of a pathogen in a medium can be identified and quantified. That is, the signature of the pathogen can be differentiated from other biological substances in the medium as well as from other pathogen. In that manner, the invention allows users to cost effectively, quickly and easily ensure that media and certain surfaces are safe and without contamination from infecting pathogen that cause diseases. With systems and methods of the invention, needless pathogen contamination is now preventable.

In an aspect, the present invention is directed to a method for determining that a medium comprises a biological substance. The method comprises directing one or more wavelengths of light that are each within a deep ultraviolet (UV) spectrum into a medium comprising a biological substance to thereby excite the biological substance in the medium. Optionally, one or more wavelengths for excitation may be outside of the deep UV region, for example at 340 nm. The method further comprises detecting emission from the excited biological substance via a plurality of semiconductor photodetectors, wherein each of the semiconductor photodetector detects only a subset of emission from the excited biological substance, thereby producing deep UV emission data; and analyzing the deep UV emission data for presence of a deep UV spectral signature indicative of the biological substance, wherein presence of the deep UV spectral signature indicates that the medium comprises a biological substance. While excitation may be in the deep UV region, emission may be in the UV region, such as in the UVA and UVB regions.

In an embodiment, the at least six semiconductor photodetectors are employed in the detecting step. In a preferred embodiment, the plurality of semiconductor photodetectors are avalanche photodiode detectors or silicon sensors.

In certain embodiments, the medium may be selected from the group consisting of a biofluid, water, an aluminum surface, a stainless steel surface, and a metallic surface.

In an exemplary embodiment, the biological substance is a pathogen. The biological substance may be a pathogen and the medium may be water in a preferred embodiment.

In certain embodiments, the method is performed in Earth's atmospheric conditions. The method may be performed outside of Earth's atmospheric conditions.

In an aspect, the present invention is directed to a system determining that a medium comprises a biological substance. The system comprises one or more excitation sources, each operating in a deep ultraviolet (UV) range for excitation of a biological substance in a medium; and a detector comprising a plurality of semiconductor photodetectors. Optionally, one or more wavelengths for excitation may be outside of the deep UV region, for example at 340 nm. The system is configured such that each semiconductor photodetector detects only a subset of emission from the excited biological substances.

Moreover, certain embodiments of the invention use emission data to determine total microbial load and bioburden measurements. The present invention comprises directing one or more wavelengths of light that are each within a deep ultraviolet (UV) spectrum into a medium comprising a biological substance to thereby excite the biological substance in the medium. Emission is detected from the excited biological substance via one or more semiconductor photodetectors, thereby producing deep UV emission data. The deep UV emission data is analyzed for presence of a deep UV spectral signature indicative of the biological substance, wherein presence of the deep UV spectral signature indicates that the medium comprises a biological substance.

The emission data may be used to determine total microbial load. Microbial load is the number and type of microorganisms contaminating an object or organism, such as non-specific biological and microbiological contamination. Total microbial load indicates the microbiology present in the sample. Emission data may be analyzed for deep UV spectral signatures indicative of microbiology. Emission data may be analyzed for deep UV spectral signatures indicative of presence and quantity of microbiology. For example, analyzing may include comparing the UV spectral signature with a library of UV spectral signatures of varying amounts and types of microbiology on or in a variety of media. Systems of the invention may indicate the total microbial load in the sample after detecting the UV spectral signatures indicative of microbiology.

In certain embodiments, the invention is used to detect total microbial load (TML). The invention is a real-time monitoring indicator of water safety complimenting the randomized spot-check of *E. coli* or Coliform test. For example, WHO and EPA waterborne disease initial screening methods do not detect non-coliform or protozoan pathogens such as *Salmonella, Cryptosporidium, Giardia*, and *Listeria*, among others. The invention can be used to detect all microbiology present in a given sample in order to provide insights that are typically undetected, even when the microbiology cannot be specified. Thus, the invention adds a complimentary layer of intelligence to current methods, such as indicating when to actually conduct a coliform test.

The emission data may be used to determine bioburden, or the number of bacteria living on a surface or within a liquid. Often, bioburden refers to the number of microorganisms on an unsterilized surface. Emission data may be analyzed for deep UV spectral signatures indicative of presence and quantity of microorganisms. For example, analyzing may include comparing the UV spectral signature with a library of UV spectral signatures of varying amounts and types of microorganisms on or in a variety of media. Systems of the invention may indicate the bioburden in the sample after detecting the UV spectral signatures indicative of the presence or quantity of microorganisms.

While excitation may be in the deep UV region, emission may be in the UV region, such as in the UVA and UVB regions. In an embodiment, the emission is in a detection range of 300-400 nm. Preferably, the at least two of the different semiconductor photodetectors overlap in the subset of emission from the excited target that each detects. In an exemplary embodiment, the system comprises at least six semiconductor photodetectors.

In certain embodiments, the system further comprises a processor configured to process data received from the plurality of semiconductor photodetectors. The processor may be integrated into the system. The processor may be remote from the system. The processor may be a computer, smart phone, or microcontroller.

In an embodiment, the system is a portable, handheld, point-and-shoot system. In an embodiment, the biological substance is a pathogen and the system is configured such that each semiconductor photodetector detects only a subset of emission from the excited pathogen to produce a deep UV spectral signature indicative of presence of the pathogen in the medium.

In an aspect, the present invention is directed to a method for identifying a pathogen in a medium. The method comprises directing one or more wavelengths of light into a medium comprising a pathogen and a non-pathogen biological substance to thereby excite the pathogen and the non-pathogen biological substance in the medium; and detecting emission using a plurality of detectors, wherein each of the semiconductor photodetectors detects different wavelengths of emission such that a spectral signature unique to the pathogen is detected and distinguished from a spectral signature of the non-pathogen biological substance, thereby identifying the pathogen in the medium.

In an embodiment, the method further comprises quantifying an amount of the pathogen in the medium. The method may further comprise generating a quality value of the medium.

In an embodiment, the non-pathogen biological substance is a protein. The pathogen may be a live pathogen. The spectral signature unique to the pathogen may be a spectral signature unique to the live pathogen. In an embodiment, the spectral signature unique to the live pathogen is detected and distinguished from a spectral signature of the pathogen when dead.

In certain embodiments, the medium is selected from the group consisting of a biofluid, water, an aluminum surface, a stainless steel surface, a granite surface, a ceramic surface, a plastic surface, and a metallic surface. The one or more wavelengths of light may be within a deep ultraviolet (UV) range. In an embodiment, the emission is detected at a range of 300-400 nm.

In an exemplary aspect, the present invention is directed to a method for identifying a plurality of pathogens in a medium. The method comprises directing one or more wavelengths of light into a medium comprising a plurality of pathogens and a non-pathogen biological substance to thereby excite the plurality of pathogens and the non-pathogen biological substance in the medium; and detecting emission using a plurality of detectors, wherein each of the semiconductor photodetectors detects different wavelengths of emission such that a spectral signature unique to each of the plurality of the pathogens is detected and the spectral signature unique to each of the plurality of the pathogens is distinguished from each other and a spectral signature of the non-pathogen biological substance, thereby identifying each of the plurality of pathogens in the medium.

In an embodiment, the method further comprises quantifying an amount of the each of the plurality of pathogens in the medium. The method may further comprise generating a quality value of the medium. In certain aspects, the non-pathogen biological substance is an amino acid. The at least pathogen one of the plurality of pathogens may be a live pathogen. The spectral signature unique to the pathogen is a spectral signature unique to the live pathogen. The spectral signature unique to the live pathogen is detected and distinguished from a spectral signature of the pathogen when dead.

In an embodiment, the medium is selected from the group consisting of a biofluid, water, an aluminum surface, a stainless steel surface, a granite surface, a ceramic surface, a plastic surface, and a metallic surface.

An embodiment of the invention is directed to a system for determining that a medium comprises a biological substance. The system comprises a housing with a built-in display, the housing sized and configured to mate with a top of a drinking glass. In certain embodiments, the housing has a unitary configuration with a conical shape. In some embodiments, the housing has a plurality of components including a base or tripod.

The system comprises one or more excitation sources disposed in the housing, each operating in a deep ultraviolet (UV) range for excitation of a biological substance in a medium. The system further comprises one or more detectors comprising a semiconductor photodetector, the one or more detectors disposed in the housing. The system is configured such that the semiconductor photodetector detects emission from the excited biological substances and displays a reading on the built-in display, wherein the reading is dependent on whether the emission exceeds a threshold detection level. The emission is in a detection range of 300-400 nm. The system is a portable, handheld, point-and-shoot system.

The system further comprises a processor configured to process data received from the semiconductor photodetector. In certain embodiments, the processor is integrated into the system. In some embodiments, the processor is remote from the system. The processor may be a computer, smart phone, or microcontroller.

The threshold detection level may be a bioburden or total microbial load. The biological substance may be a pathogen and the system may be configured such that the semiconductor photodetector detects only a subset of emission from the excited pathogen to produce a deep UV spectral signature indicative of presence of the pathogen in the medium.

In an embodiment, the invention is directed to a system for determining that a medium comprises a biological substance. The system comprises one or more excitation sources, each operating in a deep ultraviolet (UV) range for excitation of a biological substance in a medium. The system comprises one or more detectors comprising a semiconductor photodetector. In embodiments of the invention, the emission is in a detection range of 300-400 nm.

The system further comprises a housing, the one or more excitation sources and the one or more detectors disposed in the housing, and an adapter operable with the housing, the adapter configured to be releasably attachable to a supply source for the medium. In certain embodiments, the housing has a unitary configuration with a conical shape. In some embodiments, the housing has a plurality of components including a base or tripod. The system is configured such that the semiconductor photodetector detects emission from the excited biological substances and outputs a reading, the reading dependent on whether the emission exceeds a threshold detection level. In some embodiments, the adapter is releasably attachable to a pipe. In some embodiments, the adapter is a tap mount for a faucet.

The system further comprises a processor configured to process data received from the semiconductor photodetector. In certain embodiments, the processor is integrated into the system. In some embodiments, the processor is remote from the system. The processor may be a computer, smart phone, or microcontroller.

The threshold detection level may be a bioburden or total microbial load. The biological substance may be a pathogen and the system may be configured such that the semiconductor photodetector detects only a subset of emission from the excited pathogen to produce a deep UV spectral signature indicative of presence of the pathogen in the medium.

In an embodiment, the invention is directed to a method for determining that a medium comprises a biological substance. The method comprises directing one or more wavelengths of light that are each within a deep ultraviolet (UV) spectrum into a medium comprising a biological substance to thereby excite the biological substance in the medium. The method comprises detecting emission from the excited biological substance via one or more semiconductor photodetectors, each operating in a deep ultraviolet (UV) range for excitation of the biological substance in the medium, thereby producing deep UV emission data. The method further comprises analyzing the deep UV emission data for presence of a deep UV spectral signature indicative of the biological substance, wherein presence of the deep UV spectral signature indicates that the medium comprises a biological substance.

In an embodiment, the emission is in a detection range of 300-400 nm. The one or more semiconductor photodetectors is an avalanche photodiode detector or a silicon sensor.

In certain aspects, the medium is selected from the group consisting of a biofluid, water, an aluminum surface, a stainless steel surface, and a metallic surface. In some examples, the biological substance is a pathogen. In some instances, the biological substance is a pathogen and the medium is water. The method may be performed in Earth's atmospheric conditions. The method may be performed outside of Earth's atmospheric conditions.

In an embodiment, the invention is directed to a method for identifying a pathogen in a medium. The method comprises directing one or more wavelengths of light into a medium comprising a pathogen and a non-pathogen biological substance to thereby excite the pathogen and the non-pathogen biological substance in the medium; and detecting emission using one or more detectors comprising a semiconductor photodetector that detects different wavelengths of emission such that a spectral signature unique to the pathogen is detected and distinguished from a spectral signature of the non-pathogen biological substance, thereby identifying the pathogen in the medium. The method further comprises quantifying an amount of the pathogen in the medium. The method further comprises generating a quality value of the medium.

In some embodiments, the non-pathogen biological substance is a protein. In some embodiments, the pathogen is a live pathogen. In certain examples, the spectral signature unique to the pathogen is a spectral signature unique to the live pathogen. In some examples, the spectral signature unique to the live pathogen is detected and distinguished from a spectral signature of the pathogen when dead.

In certain embodiments, the medium is selected from the group consisting of a biofluid, water, an aluminum surface, a stainless steel surface, a granite surface, a ceramic surface, a plastic surface, and a metallic surface. The one or more wavelengths of light are within a deep ultraviolet (UV) range. The emission is detected at a range of 300-400 nm.

In an embodiment, the invention is directed to a method for identifying a plurality of pathogens in a medium. The method comprises directing one or more wavelengths of light into a medium comprising a plurality of pathogens and a non-pathogen biological substance to thereby excite the plurality of pathogens and the non-pathogen biological substance in the medium; and detecting emission using one or more detectors comprising a semiconductor photodetector that detects different wavelengths of emission such that a spectral signature unique to each of the plurality of the pathogens is detected and the spectral signature unique to each of the plurality of the pathogens is distinguished from each other and a spectral signature of the non-pathogen biological substance, thereby identifying each of the plurality of pathogens in the medium. The method further comprises quantifying an amount of the each of the plurality of pathogens in the medium. The method further comprises generating a quality value of the medium.

In certain embodiments, the non-pathogen biological substance is an amino acid. In certain embodiments, at least one pathogen of the plurality of pathogens is a live pathogen. The spectral signature unique to the pathogen may be a spectral signature unique to the live pathogen. In some instances, the spectral signature unique to the live pathogen is detected and distinguished from a spectral signature of the pathogen when dead.

In certain embodiments, the medium is selected from the group consisting of a biofluid, water, an aluminum surface, a stainless steel surface, a granite surface, a ceramic surface, a plastic surface, and a metallic surface. The one or more wavelengths of light are within a deep ultraviolet (UV) range. The emission is detected at a range of 300-400 nm.

BRIEF DESCRIPTION OF THE DRAWINGS

FIG. 16 shows an embodiment of a target list, or database, according to the invention.
FIG. 17 shows limits of detection with noise and without noise.
FIG. 37 shows a concentration curve.
FIG. 38 shows deconvolution of a bacterial mixture.
FIG. 45 shows results of the comparison of detection using the invention (Orb) to the Gold Standard detection.
FIG. 46 shows a selection of detection capabilities to date.

DETAILED DESCRIPTION

Figure 1:
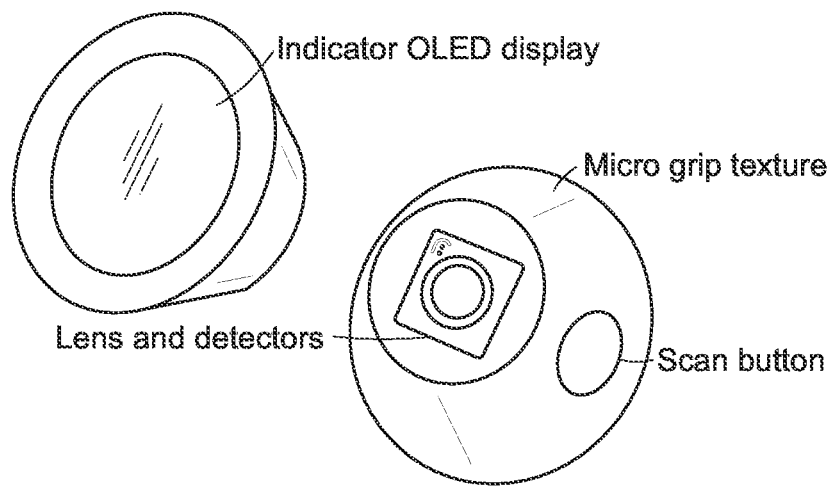
FIG. 1 shows the scanner or detector according to the present invention.

Various compounds with certain chemical structures can give strong auto-fluorescence or "native" fluorescence when excited with ultraviolet light. This can be quite strong for some interesting compounds such as plasticizers that have been identified as endocrine disrupters as well as amino acids that are found in bacterial cells. By using this phenomenon, a detection apparatus can be assembled with relatively inexpensive and robust components that use a technique that allow the final device to be non-invasive, portable, and easy to use for the consumer. Taken together, the ideal application for this technique is in the detection, identification, and quantification of one or more analytes in a medium, e.g., pathogen and other contaminating agents/analytes in water, bio-fluids, and surfaces, particularly where the current EPA/FDA approved process involves laboratory testing.

The present invention allows for detection results in seconds. In certain embodiments, devices of the present invention are portable and achieve non-contact analysis. No preparation or reagents are required, and the present invention may detect multiple contaminants. The present invention allows detection of targets in media such as water, and also allows for detection of targets on surfaces such as aluminum and stainless steel surfaces. The invention delivers real-time biological safety monitoring of process waters and surfaces for the water, pharmaceutical, semiconductor and food and beverage industries.

Hardware

With the advent of cheaper and more powerful ultraviolet light emitting diodes (UV LEDS) and sensitive detectors, the present invention may be used to identify specific molecules with a high degree of accuracy in a portable, reagent-less, non-invasive manner.

In an aspect, the present invention provides a system for detecting a target in a medium. The system comprises a light-emitting diode operating at a single wavelength in a deep ultraviolet (UV) range for excitation of a target in a medium and a plurality of semiconductor photodetectors. The system is configured such that each semiconductor photodetector detects only a subset of emission from the excited target. In a preferred embodiment, the emission is in a detection range of 300-400 nm. Deep UV is ultraviolet light below 280 nm, or ultraviolet light in the 240-280 nm range. Autofluorescence is "native" fluorescence or emission of light by biological structures when the biological structures have absorbed light or have been excited with ultraviolet light. In the present invention, the pathogens or contaminants autofluorescence after being excited by, or absorbing, deep ultraviolet light. The emission of the autofluorescence is then detected by the plurality of detectors in the range of 300-400 nm.

In certain embodiments, the system configuration for each semiconductor photodetector detecting only a subset of emission from the excited target comprises each semiconductor photodetector having a different filter applied thereto or a grating element to split the emission from the excited target such that each semiconductor photodetector detecting only a subset of emission from the excited target. In a preferred embodiment, the system comprises at least six semiconductor photodetectors. In an embodiment, the plurality of semiconductor photodetectors are avalanche photodiode detectors or silicon sensors.

In an embodiment, the system further comprises a processor configured to process data received from the plurality of semiconductor photodetectors. The processor may be integrated into the system. The processor may be remote from the system. The processor may be a computer, smart phone, or microcontroller.

In certain embodiments, the system of the present invention is a portable, handheld, point-and-shoot system.

In certain embodiments, the invention is directed to a system for detecting a target in a water source. The system comprises a light-emitting diode operating at a single wavelength in a deep ultraviolet (UV) range for excitation of a target in a water source; and a semiconductor photodetector that detects emission from the excited target and provides a readout if a detection level exceeds a threshold. The system is provided in a housing sized and configured to mate with a top of a drinking glass. In some embodiments, the housing has a unitary configuration with a conical shape. In some embodiments, the housing comprises a plurality of components including a base or tripod. The system is a portable, handheld, point-and-shoot system. The threshold detection level is a total microbial load or a bioburden. The emission is in a detection range of 300-400 nm.

The semiconductor photodetector is an avalanche photodiode detector or a silicon sensor. The system further comprises a processor configured to process data received from the semiconductor photodetector. The processor is integrated into the system. The processor is remote from the system. The processor is a computer, smart phone, or microcontroller.

In certain embodiments, the invention is directed to a system for detecting a target in a water source. The system comprises a light-emitting diode operating at a single wavelength in a deep ultraviolet (UV) range for excitation of a target in a water source; and a semiconductor photodetector that detects emission from the excited target and provides a readout if a detection level exceeds a threshold. The system is configured to be coupled in-line to the water source.

The threshold detection level is a total microbial load or a bioburden. The emission is in a detection range of 300-400 nm. The semiconductor photodetector is an avalanche photodiode detector or a silicon sensor.

The system further comprises a processor configured to process data received from the semiconductor photodetector. The processor is integrated into the system. The processor is remote from the system. The processor is a computer, smart phone, or microcontroller.

In certain embodiments, the invention is directed to a method of providing information regarding a medium. The method comprises providing a system comprising a light-emitting diode operating at a single wavelength in a deep ultraviolet (UV) range for excitation of a target in a medium, and a semiconductor photodetector that detects emission from the excited target, the system configured to be coupled in-line to the medium.

The method further comprises exposing a medium comprising one or more target analytes to at least a single wavelength in the deep UV spectrum from the light-emitting diode of the system to thereby excite the target analyte in the medium; detecting emission from the excited one or more target analytes via the semiconductor photodetector to thereby produce emission data; and outputting a read if the emission data exceeds a threshold detection level, thereby providing information regarding the medium. The method further comprises displaying on a graphical user interface results of the processing step.

Processing the emission data comprises identifying presence of one or more target analytes in the medium. Processing the emission data further comprises identifying the one or more target analytes in the medium. Processing the emission data further comprises quantifying the one or more target analytes in the medium.

The medium is selected from the group consisting of a biofluid, water, an aluminum surface, a stainless steel surface, a granite surface, a ceramic surface, a plastic surface, and a metallic surface. The method may be performed in Earth's atmospheric conditions. The method may be performed outside of Earth's atmospheric conditions.

In some embodiments, the threshold detection level is a total microbial load or a bioburden. The target analyte is selected from the group consisting of a microorganism, a biomolecule, and a chemical. In some embodiments, the medium is water and the target analyte is one or more pathogens.

In certain embodiments, the invention is directed to a method of providing information regarding a medium. The method comprises providing a system comprising a light-emitting diode operating at a single wavelength in a deep ultraviolet (UV) range for excitation of a target in a medium, and a semiconductor photodetector that detects emission from the excited target, the system provided in a housing sized and configured to mate with a top of a drinking glass. In some embodiments, the housing has a unitary configuration with a conical shape. In certain embodiments, the housing comprises a plurality of components including a base or tripod. The method comprises exposing a medium comprising one or more target analytes to at least a single wavelength in the deep UV spectrum from the light-emitting diode of the system to thereby excite the target analyte in the medium. The method comprises detecting emission from the excited one or more target analytes via the semiconductor photodetector to thereby produce emission data. The method further comprises outputting a read if the emission data exceeds a threshold detection level, thereby providing information regarding the medium. In some embodiments, the method further comprises displaying on a graphical user interface results of the processing step.

In some embodiments, the threshold detection level is a total microbial load or a bioburden. The medium may be selected from the group consisting of a biofluid, water, an aluminum surface, a stainless steel surface, a granite surface, a ceramic surface, a plastic surface, and a metallic surface. The target analyte may be selected from the group consisting of a microorganism, a biomolecule, and a chemical. In some examples, the medium is water and the target analyte is one or more pathogens. The method may be performed in Earth's atmospheric conditions. The method may be performed outside of Earth's atmospheric conditions.

In an embodiment, processing the emission data comprises identifying presence of one or more target analytes in the medium. Processing the emission data further comprises identifying the one or more target analytes in the medium. Processing the emission data further comprises quantifying the one or more target analytes in the medium.

In certain embodiments, the invention is directed to a system for determining that a medium comprises a biological substance. The system comprises a housing with a built-in display, the housing sized and configured to mate with a top of a drinking glass. In certain embodiments, the housing has a unitary configuration with a conical shape. In some embodiments, the housing has a plurality of components including a base or tripod.

The system comprises one or more excitation sources disposed in the housing, each operating in a deep ultraviolet (UV) range for excitation of a biological substance in a medium. The system further comprises one or more detectors comprising a semiconductor photodetector, the one or more detectors disposed in the housing. The system is configured such that the semiconductor photodetector detects emission from the excited biological substances and displays a reading on the built-in display, wherein the reading is dependent on whether the emission exceeds a threshold detection level. The emission is in a detection range of 300-400 nm. The system is a portable, handheld, point-and-shoot system.

The system further comprises a processor configured to process data received from the semiconductor photodetector. In certain embodiments, the processor is integrated into the system. In some embodiments, the processor is remote from the system. The processor may be a computer, smart phone, or microcontroller.

The threshold detection level may be a bioburden or total microbial load. The biological substance may be a pathogen and the system may be configured such that the semiconductor photodetector detects only a subset of emission from the excited pathogen to produce a deep UV spectral signature indicative of presence of the pathogen in the medium.

In an embodiment, the invention is directed to a system for determining that a medium comprises a biological substance. The system comprises one or more excitation sources, each operating in a deep ultraviolet (UV) range for excitation of a biological substance in a medium. The system comprises one or more detectors comprising a semiconductor photodetector. In embodiments of the invention, the emission is in a detection range of 300-400 nm.

The system further comprises a housing, the one or more excitation sources and the one or more detectors disposed in the housing, and an adapter operable with the housing, the adapter configured to be releasably attachable to a supply source for the medium. In certain embodiments, the housing has a unitary configuration with a conical shape. In some embodiments, the housing has a plurality of components including a base or tripod. The system is configured such that the semiconductor photodetector detects emission from the excited biological substances and outputs a reading, the reading dependent on whether the emission exceeds a threshold detection level. In some embodiments, the adapter is releasably attachable to a pipe. In some embodiments, the adapter is a tap mount for a faucet.

The system further comprises a processor configured to process data received from the semiconductor photodetector. In certain embodiments, the processor is integrated into the system. In some embodiments, the processor is remote from the system. The processor may be a computer, smart phone, or microcontroller.

The threshold detection level may be a bioburden or total microbial load. The biological substance may be a pathogen and the system may be configured such that the semiconductor photodetector detects only a subset of emission from the excited pathogen to produce a deep UV spectral signature indicative of presence of the pathogen in the medium.

In an embodiment, the invention is directed to a system for determining that a medium comprises a biological substance. The system comprises one or more excitation sources, each operating in a deep ultraviolet (UV) range for excitation of a biological substance in a medium. The system comprises one or more detectors comprising a semiconductor photodetector. In embodiments of the invention, the emission is in a detection range of 300-400 nm.

The system further comprises a housing, the one or more excitation sources and the one or more detectors disposed in the housing, and an adapter operable with the housing, the adapter configured to be releasably attachable to a supply source for the medium. The system is configured such that the semiconductor photodetector detects emission from the excited biological substances and outputs a reading, the reading dependent on whether the emission exceeds a threshold detection level.

In certain embodiments, the housing has a unitary configuration with a conical shape. In some embodiments, the housing has a plurality of components including a base or tripod. In some embodiments, the adapter is releasably attachable to a pipe. In some embodiments, the adapter is a tap mount for a faucet.

The system further comprises a processor configured to process data received from the semiconductor photodetector. In certain embodiments, the processor is integrated into the system. In some embodiments, the processor is remote from the system. The processor may be a computer, smart phone, or microcontroller.

The threshold detection level may be a bioburden or total microbial load. The biological substance may be a pathogen and the system may be configured such that the semiconductor photodetector detects only a subset of emission from the excited pathogen to produce a deep UV spectral signature indicative of presence of the pathogen in the medium.

In an embodiment, the invention is directed to a method for determining that a medium comprises a biological substance. The method comprises directing one or more wavelengths of light that are each within a deep ultraviolet (UV) spectrum into a medium comprising a biological substance to thereby excite the biological substance in the medium.

The method comprises detecting emission from the excited biological substance via one or more semiconductor photodetectors, each operating in a deep ultraviolet (UV) range for excitation of the biological substance in the medium, thereby producing deep UV emission data. The method further comprises analyzing the deep UV emission data for presence of a deep UV spectral signature indicative of the biological substance, wherein presence of the deep UV spectral signature indicates that the medium comprises a biological substance.

In an embodiment, the emission is in a detection range of 300-400 nm. The one or more semiconductor photodetectors is an avalanche photodiode detector or a silicon sensor.

In certain aspects, the medium is selected from the group consisting of a biofluid, water, an aluminum surface, a stainless steel surface, and a metallic surface. In some examples, the biological substance is a pathogen. In some instances, the biological substance is a pathogen and the medium is water. The method may be performed in Earth's atmospheric conditions. The method may be performed outside of Earth's atmospheric conditions.

In an embodiment, the invention is directed to a method for identifying a pathogen in a medium. The method comprises directing one or more wavelengths of light into a medium comprising a pathogen and a non-pathogen biological substance to thereby excite the pathogen and the non-pathogen biological substance in the medium; and detecting emission using one or more detectors comprising a semiconductor photodetector that detects different wavelengths of emission such that a spectral signature unique to the pathogen is detected and distinguished from a spectral signature of the non-pathogen biological substance, thereby identifying the pathogen in the medium. The method further comprises quantifying an amount of the pathogen in the medium. The method further comprises generating a quality value of the medium.

In some embodiments, the non-pathogen biological substance is a protein. In some embodiments, the pathogen is a live pathogen. In certain examples, the spectral signature unique to the pathogen is a spectral signature unique to the live pathogen. In some examples, the spectral signature unique to the live pathogen is detected and distinguished from a spectral signature of the pathogen when dead.

In certain embodiments, the medium is selected from the group consisting of a biofluid, water, an aluminum surface, a stainless steel surface, a granite surface, a ceramic surface, a plastic surface, and a metallic surface. The one or more wavelengths of light are within a deep ultraviolet (UV) range. The emission is detected at a range of 300-400 nm.

In an embodiment, the invention is directed to a method for identifying a plurality of pathogens in a medium. The method comprises directing one or more wavelengths of light into a medium comprising a plurality of pathogens and a non-pathogen biological substance to thereby excite the plurality of pathogens and the non-pathogen biological substance in the medium; and detecting emission using one or more detectors comprising a semiconductor photodetector that detects different wavelengths of emission such that a spectral signature unique to each of the plurality of the pathogens is detected and the spectral signature unique to each of the plurality of pathogens is distinguished from each other and a spectral signature of the non-pathogen biological substance, thereby identifying each of the plurality of pathogens in the medium. The method further comprises quantifying an amount of the each of the plurality of pathogens in the medium. The method further comprises generating a quality value of the medium.

In certain embodiments, the non-pathogen biological substance is an amino acid. In certain embodiments, at least one pathogen of the plurality of pathogens is a live pathogen. The spectral signature unique to the pathogen may be a spectral signature unique to the live pathogen. In some instances, the spectral signature unique to the live pathogen is detected and distinguished from a spectral signature of the pathogen when dead.

In certain embodiments, the medium is selected from the group consisting of a biofluid, water, an aluminum surface, a stainless steel surface, a granite surface, a ceramic surface, a plastic surface, and a metallic surface. The one or more wavelengths of light are within a deep ultraviolet (UV) range. The emission is detected at a range of 300-400 nm.

Figure 22:
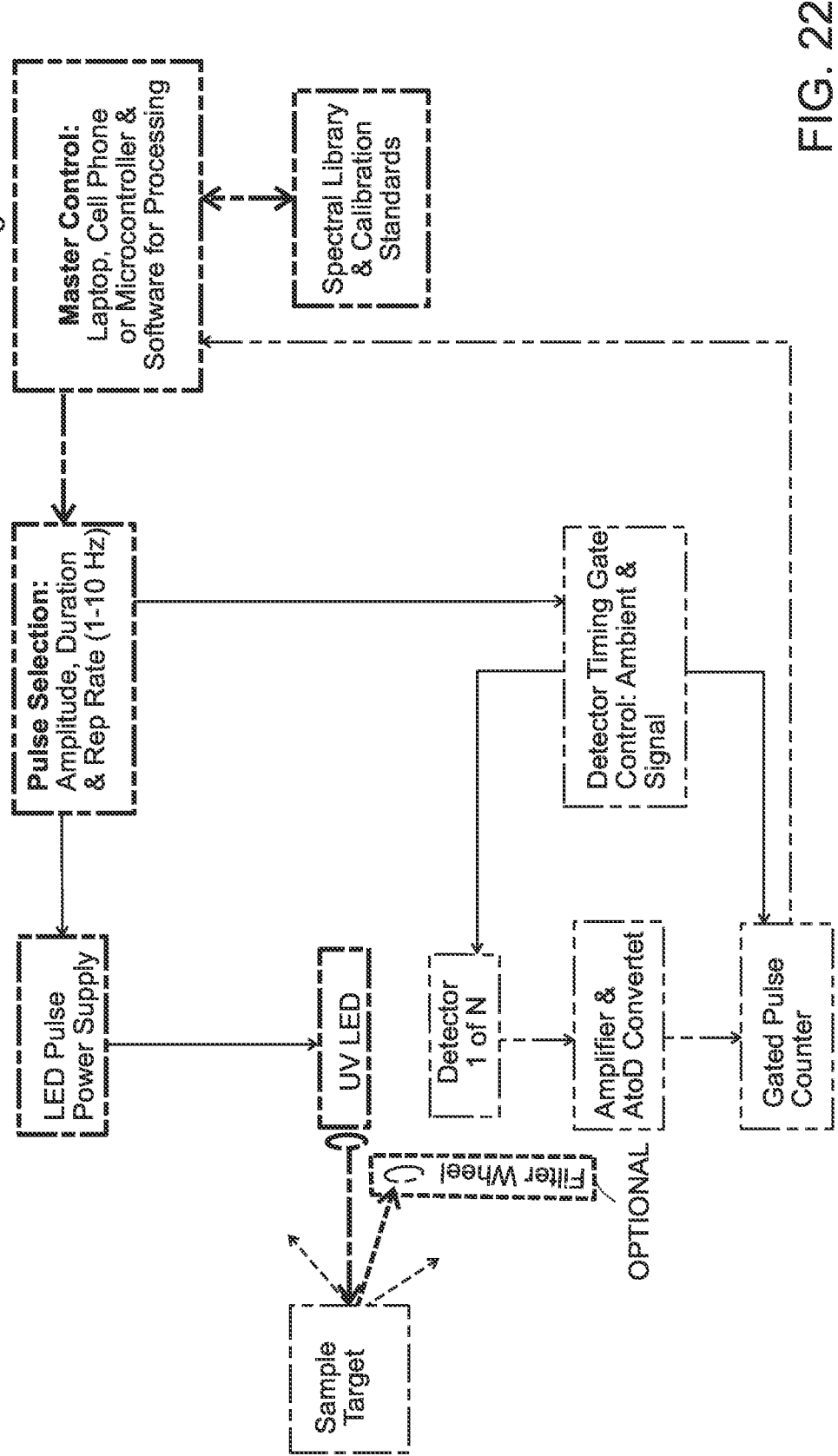
FIG. 22 shows the system block diagram of the present invention.

As shown in FIG. 22, the system block diagram depicts a sample target being subjected to UV LED. Detector 1 of N detectors detects the signal from the sample target and sends the signal to the Amplifier & AtoD (analog to digital) Converter to be amplified and converted to digital. The signal then goes to the gated pulse controller and then on to the master control. The master control may be any suitable means and preferably may be a laptop, cell phone, or microcontroller and software for processing. The master control is in communication with the spectral library and the calibration standards of the present invention. The master control may send results via Bluetooth LE, smartphones, and personal computers. The master control also communicates with the pulse selection for amplitude, duration and rep rate (1-10 Hz). The pulse selection communications to the LED pulse power supply which inputs to the UV LED. The pulse selection also communicates with the detector timing gate control for the ambient and signal timing. A filter wheel may optionally be arranged between the sample target and Detector 1 of N detectors.

Figure 23:
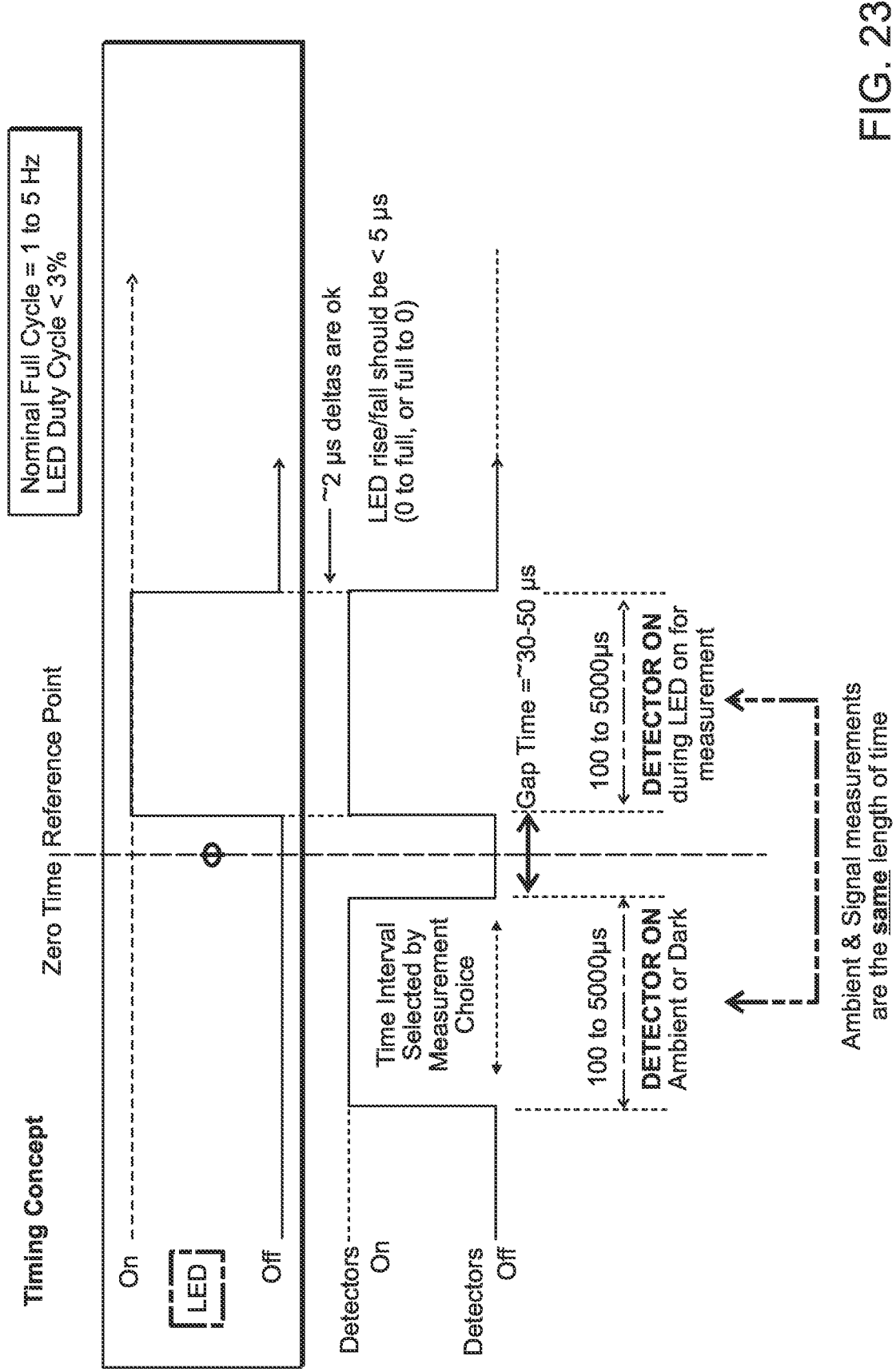
FIG. 23 shows the timing concept of the present invention.

The timing concept of the present invention is shown in FIG. 23. A nominal full cycle is 1 to 5 Hz. the LED duty cycle is less than 3%. At the zero time reference point, the LED and Detectors are OFF. Once the LED and Detectors are ON, the LED rise/fall should be less than 5 μs, with 0 to full, or full to 0 as options. The ambient and signal measurements are the same length of time.

Multiple system configurations are further discussed and exemplified herein and the skilled artisan will appreciate that the configurations are exemplary and non-limiting embodiments of the invention. In a particular exemplary embodiment, the present invention identifies and quantifies certain targets using a single wavelength excitation and six (6) channel detection between the 300-400 nm range. This involves characterizing the spectral properties of these targets. In certain embodiments, the invention uses single channel detection, or 1 channel detection. Single channel detection allows for indication of presence or absence of a biological substance or microorganism.

In order to determine the feasibility of using native fluorescence to detect potential targets at low concentrations, a screening protocol was constructed to determine various criteria to identify possible targets. A photometric standard was created to correlate various detection schemes (spectrophotometers/various detectors/various optical layout), which is not commercially available. This allows for determination of possible limits of detection (in parts per million (ppm)/parts per billion) depending on hardware parameters (PMT/Si Detector). The potential targets may be determined (see FIG. 16 for exemplary targets). Potential challenges addressed and overcome include environmental factors (pH, salt, temperature), and quenching at lower concentrations than previously reported.

A model was created based on the concentration study of individual targets in tap water. The robustness of the model was tested by artificially added noise and determining limits of detection. A simulated engine was created based on real data to generate initial hardware parameters (band passes, optimized laser excitation signal/noise, etc.) and test robustness of initial quantification algorithm. From samples made in lab, BPA was able to be detected and quantified down to 0.023 ppm cross-validated with optimized laser excitation and band passes. A key finding for the algorithm development was to be able to construct a library for quantification of new samples. The calibration library in house may quantify BPA down to 0.023 ppm in water with a similar environment (FIG. 17).

Figure 18:
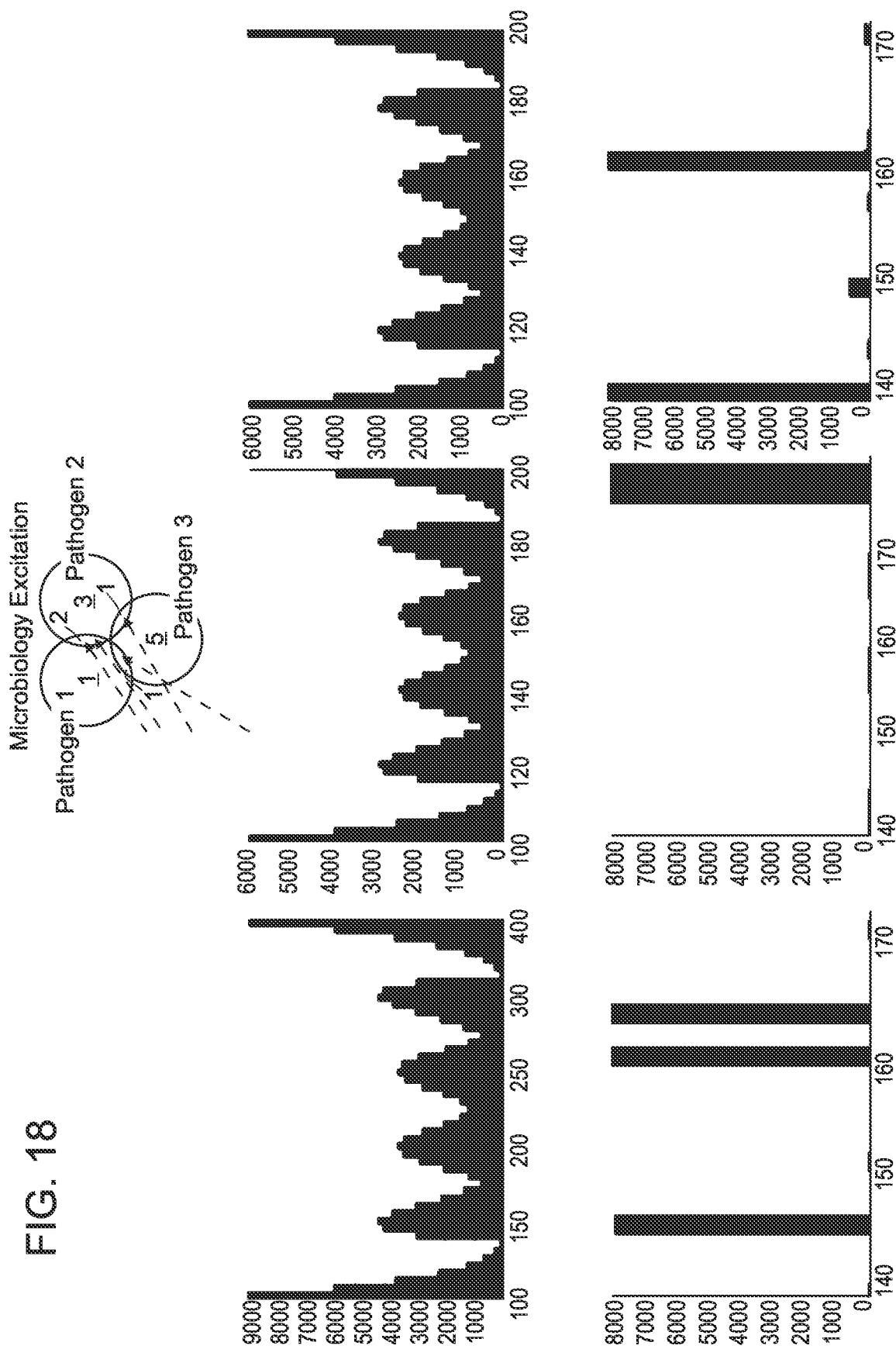
FIG. 18 shows the signatures for filtering out microbiology.

The bandpass configuration was determined that would separate out microbiology from each other and from amino acid signatures. Certain excitations separate out different microbiological strains from each other as well as raw amino acid signatures using six channel detection (FIG. 18).

Figure 19:
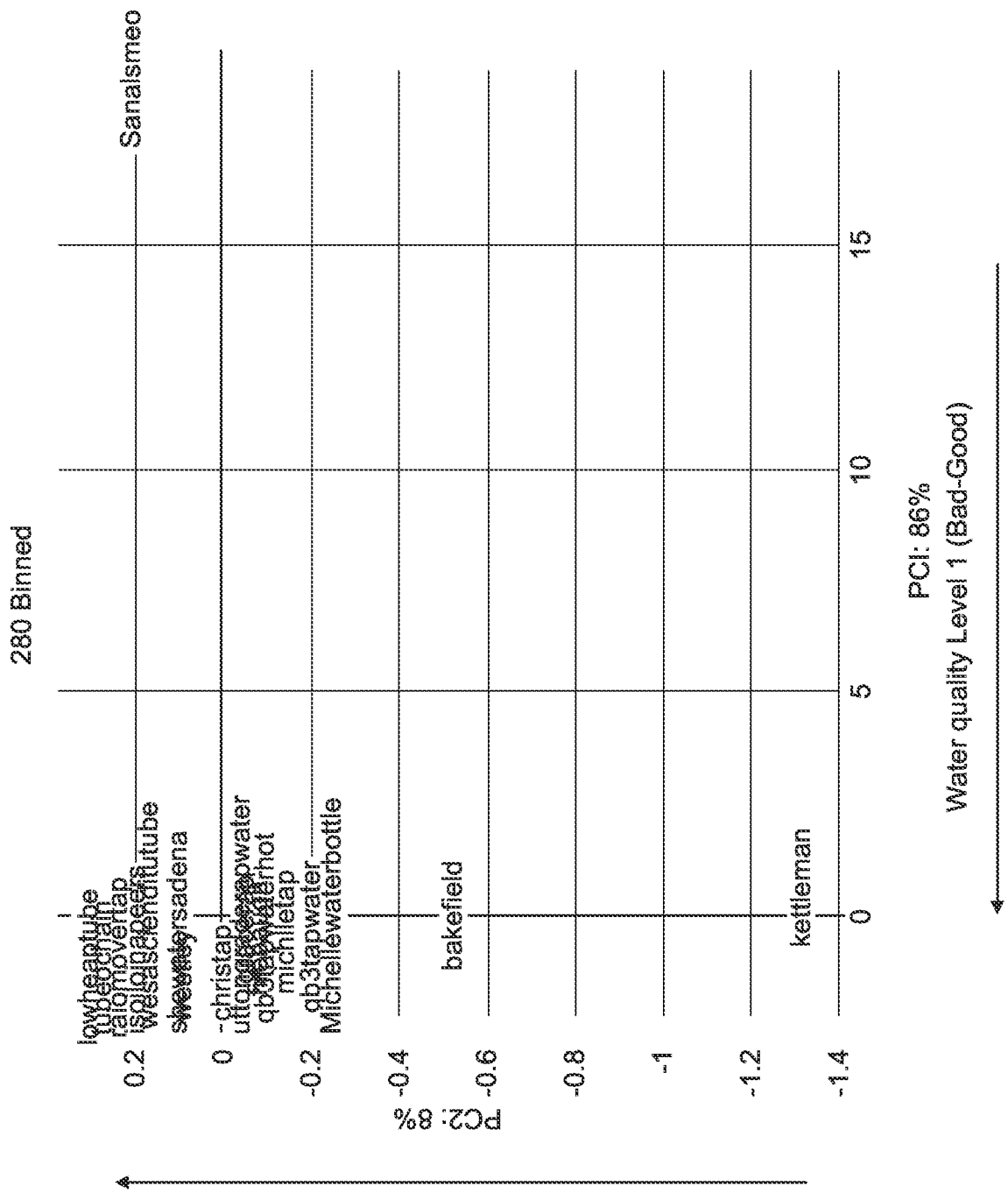
FIG. 19 shows the water quality scaling.

Water quality may be discerned with a single excitation and six channel detection of native auto fluorescence. Various hardware configurations provide the water quality information. Final determination of water quality may be verified by a water lab (FIG. 19).

In certain embodiments, the hardware specifications included the following examples for LED and detectors. As an exemplary embodiment, the LED was selected from continuous mode—100 mA~1 mW and pulsed mode, 4 Hz, 2% Duty cycle (5 ms on). The max drive current was ~350 mA with Thor Lab power supply and Rigol pulse generator.

Figure 20:
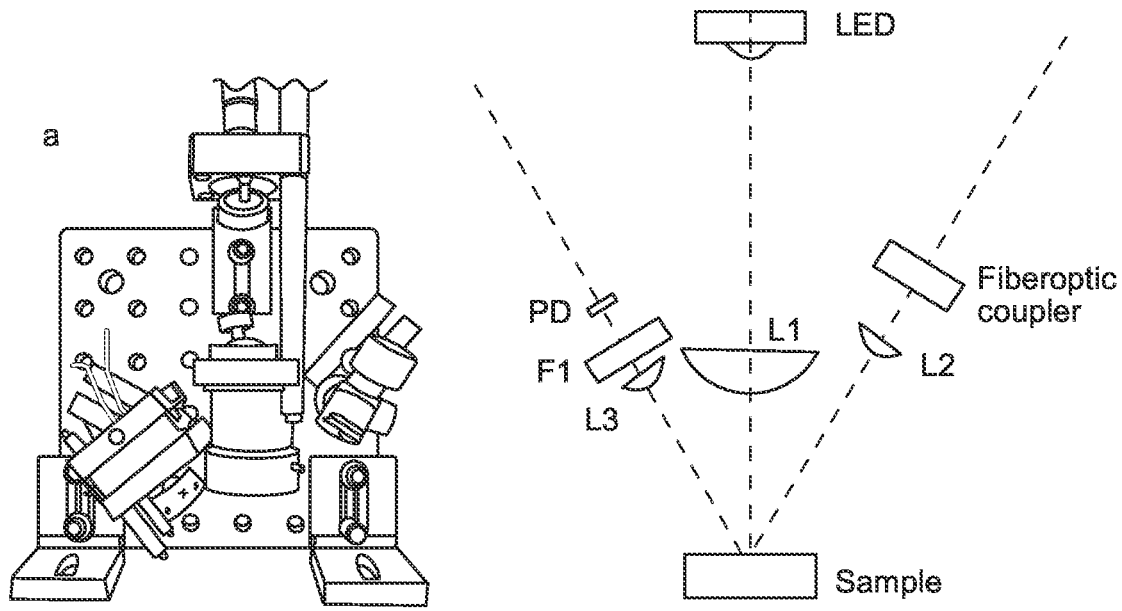
FIG. 20 shows an embodiment of hardware specifications according to the breadboard setup.

As an exemplary embodiment, the detector was selected from Hamamatsu S12698-01 photodiode, Hamamatsu MPPC, and STS-UV Ocean optics fiber coupled spectrometer (FIG. 20).

Figure 21:
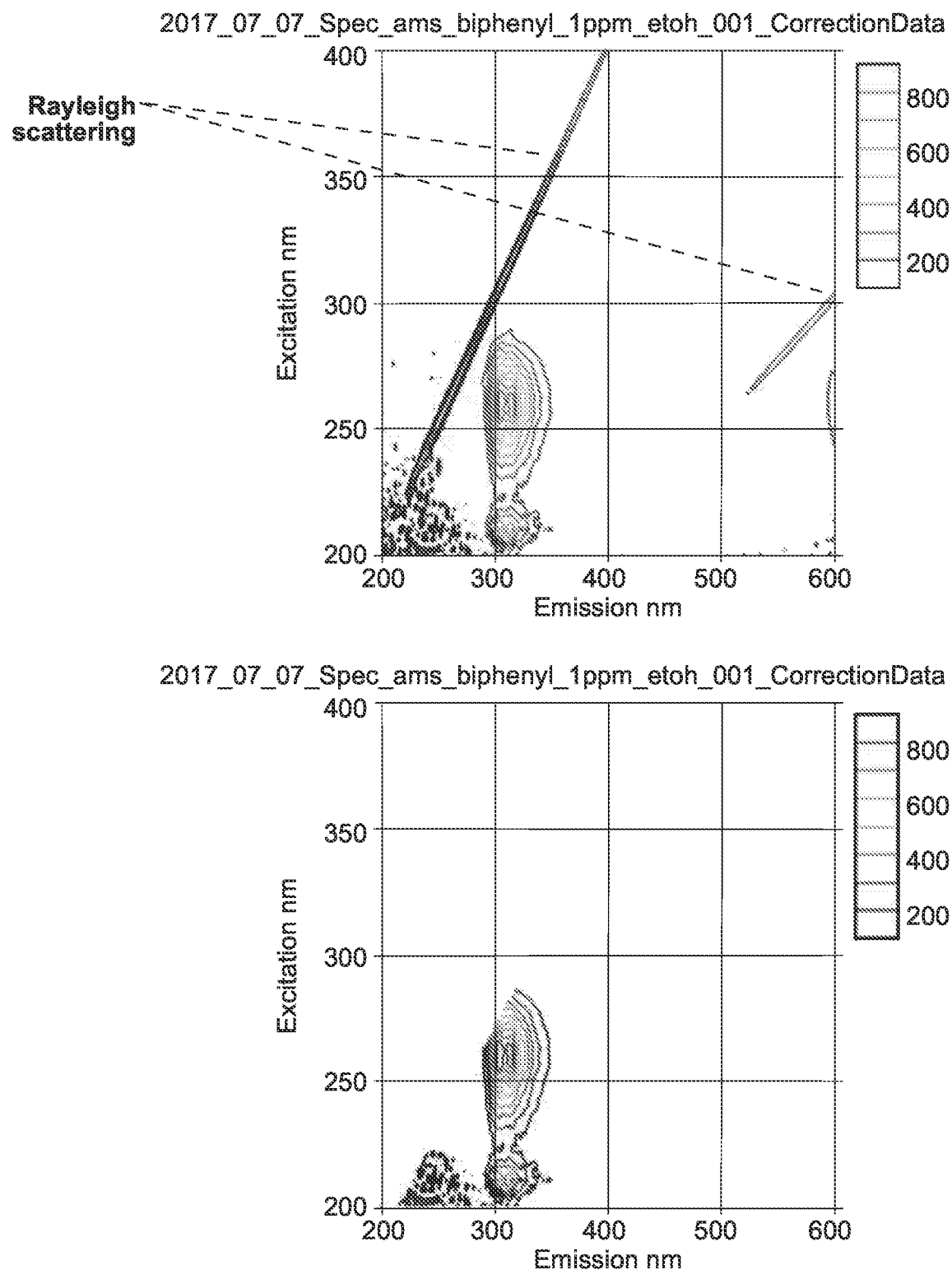
FIG. 21 shows the reference calibration target of biphenyl.

The configuration utilizes the front surface detection with an LED light source (278 nm) focused onto a cuvette holder and detector assembly placed at approximately 35 degrees away from the incoming beam to collect the fluorescence light. With this configuration, the resulting fluorescence output of the standard biphenyl in ethanol was determined in absolute values (uW/nanojoules). Therefore, the range of signals expected to be found as a function of target of interest (FIG. 21) was calculated. The silicon detector was suitable and a preferable detector may be the MPPC (APD). At 1 mW (100 mA) a sample, $10^2$ CFU (colony forming units of bacteria) produce about 3 pW of fluorescence in the 300-400 nm range. The angle dependence may further be optimized.

In certain embodiments, a grating system may be used instead of filters and how the light is split and filtered would change slightly. Using a grating option may allow access to more wavelengths of interest.

Algorithms and Software

The present invention also uses algorithms in detection, identification, and quantification of target analytes. The initial target screens for the algorithm include determination of whether the target fluoresce in the region of interest, e.g. in water, whether the fluorescence is strong enough, e.g. to EPA/FDA limits, and whether samples contaminated with targets that are indicative of real world scenarios may be experimentally created.

Identification, classification, and quantification are then based on fluorescence spectrum. This requires a model based on experimentally derived data. The data in the model is correlated to and indicative of real world scenarios in order to ensure robustness and high confidence levels of the models. For example, fluorescence can change based on temperature/pH/salt other molecular interactions and models of the invention account for various conditions (i.e. only tap water, only pool water, etc.).

In an embodiment of the present invention, an algorithm may used by a user who identifies a source for the medium. The sample may then be scanned and compared to an in-house database of sources. If the source is within the "threshold", the water quality value may be reported. If the source is outside of the "threshold", the source may be identified as an outlier. The source may then be compared to an in-house database of contaminants, which is in communication with the samples in the contaminant and chemical libraries. If the contaminant is identified, then the contaminant may further be quantified.

Figure 24:
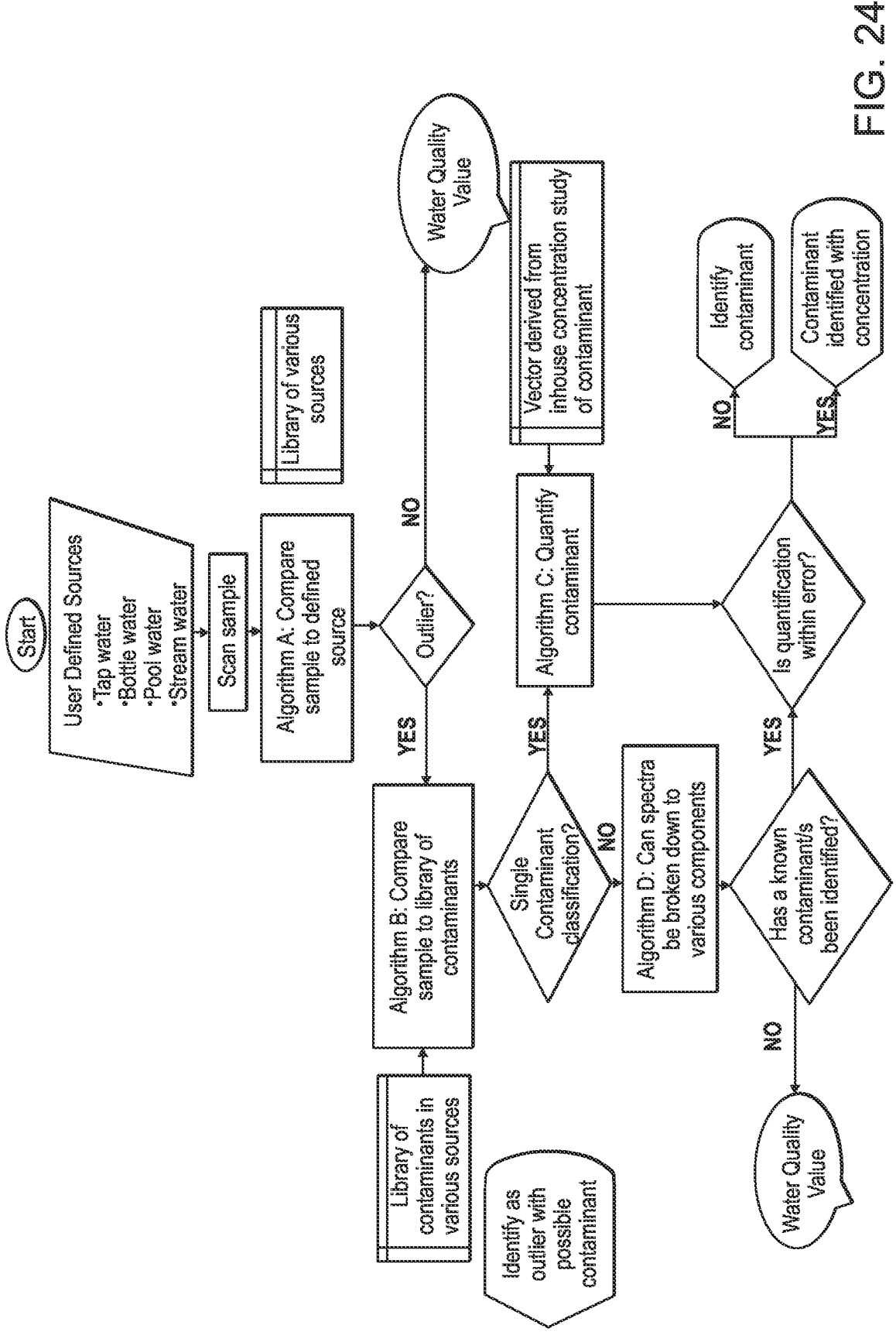
FIG. 24 shows an embodiment of an algorithm used in the present invention.

FIG. 24 shows an embodiment of an algorithm used in the present invention. The user identifies a source for the medium. The sample is scanned. The sample is then compared to defined source, a step which uses a library of sources that is already in-house. If the sample is not detected as an outlier, then the water quality value is reported. If the sample is detected as an outlier, the sample is compared to the library of contaminants, which uses a library of contaminants in various sources. If there is a single contaminant classification, then quantification commences using the in-house concentration study of the contaminant. If there was no single contaminant classification, then it is considered whether the spectra may be broken down to various components. If a known contaminant has not been identified, then a water quality value is output. If a known contaminant has been identified, then a determination of whether the quantification is within error is made. If the quantification is within error, then the contaminant is identified with a concentration. If the quantification is not within error, then merely the contaminant is identified.

Various known statistical pattern recognition methods can be used in conjunction with the present invention. For example, the following statistical methods, training sets, machine learning techniques, and comparisons to known spectra may be used.

An important feature of the methods of the invention is the ability to analyze heterogeneous samples using a fluorescence or an absorption spectrum. Fluorescence microscopy measures the fluorescence of a particular compound when given a particular wavelength. As such, the wavelength that reaches the detector is a different wavelength than used to shine the sample. Fluorescent compounds can absorb light at a particular wavelength and emit light at a higher wavelength, with some energy being lost by the compound to the surroundings. Absorbance spectroscopy measures how much of a particular wavelength of light gets absorbed by a sample. It's usually used to measure the concentration of a compound in a sample. As such, the more light that is absorbed, the higher the concentration of the compound in the sample.

The methods for analyzing the fluorescence or absorption spectrum are based upon the principles that each element in a mixture has its own spectrum and that each element has a specific absorption coefficient. The methods of the invention then correlate concentration with absorption. Particularly, the concentration of a compound can be determined with the knowledge of the compound's absorption coefficient. This relationship, in the most basic sense, can be illustrated by Beer's Law:

$$A = \varepsilon b c,$$

wherein A is absorbance, c is concentration (mol/L; M), b is pathlength, and $\varepsilon$ is the molar absorptivity (or extinction coefficient). Molar absorptivity is the characteristic of a substance that tells how much light is absorbed at a particular wavelength.

When measuring the fluorescence or absorption of a heterogeneous mixture, the sum of the absorption coefficient values for each element is measured at the same time. Thus, in order to determine the concentration, the linear combination of all spectra of the elements needs to be determined. The analysis then takes into account the interaction of elements with one another. The analysis then accounts for the fact that despite each element having a different spectrum, their optical absorbance can be the same. For example, one element may be present at 1 mM and another may also be present at 1 mM, both of which can be 1000 times less than the total value, or signal, of the mixture.

In one embodiment, deconvolution can be used to enable determination of concentrations. Deconvolution is an algorithm-based process used to reverse the effects of convolution on recorded data. See, e.g., O'Haver T. "Intro to Signal Processing—Deconvolution". University of Maryland at College Park. Retrieved 2016 Sep. 13, the content of which is incorporated by reference herein in its entirety. In general, the object of deconvolution is to find the solution of a convolution equation of the form: $f*g=h$, wherein h is some recorded value, and f is the desired value, but has been convolved with some other value g before it was recorded. The function g might represent the interaction between two elements. If g is known, then deterministic deconvolution can be performed. However, if g is not known in advance, then it will need to be estimated using, for example, statistical estimation. In actual practice, the situation is usually closer to: $(f*g)+\varepsilon=h$, wherein $\varepsilon$ is noise that has entered the recorded value. The lower the signal-to-noise ratio, the worse the estimate of the deconvolved value will be.

Methods for deconvoluting the data in accordance with the present disclosure include the use of, for example, principal component analysis (PCA). PCA is a statistical procedure that reduces the dimensionality of a data set by transforming the data to a new set of variable (principal components) that summarize the features of the data. See, for example, Jolliffe, 1986, Principal Component Analysis, Springer, New York. PCA uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables. The first few principal components ("PCs") capture most of the variation in the data set. In contrast, the last few PCs are often assumed to capture only the residual 'noise' in the data. PCA is discussed in more detail below with respect to use of databases in the analysis of data. It is also to be understood that other statistical analysis methods known in the art, such as those discussed in more detail below, can be used. Exemplary analyses are also described below.

In the present invention, the presence of a target analyte and its concentration may be reported. In certain embodiments, the methods of the invention can involve the use of a computer system (described in more detail below) to generate a report that includes a determination of the presence of and concentration of the target analyte. The computer system may perform one or more of the following steps: analyzing the sample to provide spectral data on the one or more target analytes received by the single detector, retrieving known spectral and concentration data, applying the known data to the spectral data received by the detector, and generating a report comprising the concentration of the one or more target analytes. The report may be sent to an output device such as a display monitor or a printer.

Converting a Fluorescence or an Absorption Spectrum to a Concentration Reading

Sample analysis results are generally reported in concentrations of different analytes in a sample. The present disclosure provides for a method in which spectral data can be converted into concentration for a target analyte through the comparison of the spectral data to a database comprising known spectra already associated with concentration levels of the target analyte. Because methods of the present invention may involve the use of a single detector that receives a light beam after it has passed through the sample, the spectral data may include total absorption or fluorescence data. Optionally, more than one detector, e.g. inclusive up to at least six or more detectors, may be used. Typically, when converting spectral data to concentration, careful measurement of a "training set" of samples is performed. A mathematical multivariate model is then constructed for individual components to be eventually used to evaluate unknown concentrations.

In certain embodiments, the database will contain chemical composition and spectral data from a training set. The training set can comprise a number of samples from which the chemical composition and spectral behavior are known. Chemical composition data can be determined through any means known in the art, such as, for example, a chemical component analyzer (CCA). Spectral behavior can be determined through any means known in the art, including the apparatuses and methods described herein.

Using the spectral data obtained, the concentration of the components (e.g. elements of blood plasma) can be determined. This information is compiled in a database and absorption or fluorescence/concentration curves for the various components/elements can be determined and also contained in the database.

Once the database is compiled, the concentration of one or more target analytes in a heterogeneous sample can be determined. This is done by comparing the spectral data obtained according to the present disclosure to the database comprising the known spectra already associated with concentration levels of the target analyte.

This aspect of the present disclosure is especially amenable for implementation using a computer. The computer or CPU is able to compare the spectral data of the target analyte(s) to the reference spectral data to thereby provide the concentration of the target analyte(s). Such systems generally include a central processing unit (CPU) and storage coupled to the CPU. The storage stores instructions that when executed by the CPU, cause the CPU to accept as input, spectral data obtained by the detector. The executed instructions also cause the computer to provide the concentration of the target analyte as a result of inputting the sample data into an algorithm, or pattern recognition platform, trained on the reference set of known spectral data.

In certain embodiments, the reference set is stored at a remote location separate from the computer and the computer communicates across a network to access the reference set in order to determine the concentration. In other embodiments, the reference set is stored locally within the computer and the computer accesses the reference set within the computer in order to make the determination.

The pattern recognition platform can be based on any appropriate pattern recognition method that is capable of receiving input data representative of a spectral data from the sample being analyzed and providing the concentration of the target analyte in the sample as an output. The pattern recognition program is trained with training data from a reference set of known spectral data and concentrations from various analytes. In some embodiments, a test sample having known concentration and spectral data can be used to test the accuracy of the platform recognition platform obtained using the training data.

Various known statistical pattern recognition methods can be used in conjunction with the present disclosed methods. Suitable statistical methods include, without limitation, principal component analysis (PCA), logic regression, ordinal logistic regression, linear or quadratic discriminant analysis, clustering, nearest neighbor classifier analysis, and Cox Proportional Handling. Non-limiting examples of implementing particular pattern recognition platforms using the various statistical are provided herein.

In some embodiments, the pattern recognition platform is based on a regression model, preferably a logistic regression model. Some embodiments of the present invention provide generalizations of the logistic regression model that handle multicategory (polychotomous) responses. Such embodiments can be used to discriminate between three or more elements. Such regression models use multicategory logit models that simultaneously refer to all pairs of categories, and describe the odds of response in one category instead of another. Once the model specifies logits for a certain (J–1) pairs of categories, the rest are redundant. See, for example, Agresti, An Introduction to Categorical Data Analysis, John Wiley & Sons, Inc., 1996, New York, Chapter 8, which is hereby incorporated by reference.

Linear discriminant analysis (LDA) attempts to classify sample according to its elemental composition based on certain spectral properties. In other words, LDA tests whether measured spectral data predicts categorization. LDA typically requires continuous independent variables and a dichotomous categorical dependent variable. In the present disclosure, the spectral data for select wavelengths across a number of elements in the training population serve as the requisite continuous independent variables. The concentration of each of the elements of the training population serves as the dichotomous categorical dependent variable.

LDA seeks the linear combination of variables that maximizes the ratio of between-group variance and within-group variance by using the grouping information. Implicitly, the linear weights used by LDA depend on how the spectral data for a wavelength separates between, for example, two different elements and how the spectral data correlates with spectral data for other wavelengths. For example, LDA can be applied to the data matrix of the N members (e.g. elements) in the training sample by K wavelengths in a number of wavelengths described in the present invention. Then, the linear discriminant of each member of the training population is plotted. Ideally, those members of the training population representing a first subgroup (e.g. a first element) will cluster into one range of linear discriminant values and those members of the training population representing a second subgroup (e.g. a second element) will cluster into a second range of linear discriminant values. The LDA is considered more successful when the separation between the clusters of discriminant values is larger. For more information on linear discriminant analysis, see Duda, Pattern Classification, Second Edition, 2001, John Wiley & Sons, Inc; and Hastie, 2001, The Elements of Statistical Learning, Springer, New York; Venables & Ripley, 1997, Modern Applied Statistics with s-plus, Springer, New York.

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

In some embodiments of the present disclosure, decision trees are used to classify elements using spectral data for a selected set of wavelengths. Decision tree algorithms belong to the class of supervised learning algorithms. The aim of a decision tree is to induce a classifier (a tree) from real-world example data. This tree can be used to classify unseen examples (determine elements in a sample of unknown composition) which have not been used to derive the decision tree. A decision tree is derived from training data. An example contains values for the different attributes and what class the example belongs. In one embodiment, the training data is spectral data from a number of wavelengths across the training population (e.g. various elements)

In general there are a number of different decision tree algorithms, many of which are described in Duda, Pattern Classification, Second Edition, 2001, John Wiley & Sons, Inc. Decision tree algorithms often require consideration of feature processing, impurity measure, stopping criterion, and pruning. Specific decision tree algorithms include, cut are not limited to classification and regression trees (CART), multivariate decision trees, ID3, and C4.5.

In one approach, when an exemplary embodiment of a decision tree is used, the spectral data for a representative number of wavelengths across a training population is standardized to have mean zero and unit variance. The members (e.g. elements) of the training population are randomly divided into a training set and a test set. For example, in one embodiment, two thirds of the members of the training population are placed in the training set and one third of the members of the training population are placed in the test set. The spectral data for a representative number of wavelengths are used to construct the decision tree. Then, the ability for the decision tree to correctly classify members in the test set is determined. In some embodiments, this computation is performed several times for a given number of wavelengths. In each iteration of the computation, the members of the training population are randomly assigned to the training set and the test set. Then, the quality of the combination of traits is taken as the average of each such iteration of the decision tree computation.

In some embodiments, the spectral data across a representative number of wavelengths is used to cluster a training set. For example, consider the case in which ten wavelengths are used. Each member m (e.g. element) of the training population will have absorption or fluorescence/concentration values for each of the ten wavelengths. Such values from a member m in the training population define the vector:

$X_{1m}\ X_{2m}\ X_{3m}\ X_{4m}\ X_{5m}\ X_{6m}\ X_{7m}\ X_{8m}\ X_{9m}\ X_{10m}$ where $X_{im}$ is the fluorescence or absorbance/concentration of the ith wavelength in element m. If there are m elements in the training set, selection of i wavelengths will define m vectors. Those members of the training population that exhibit similar absorption or fluorescence/concentration curves across the training group will tend to cluster together.

A particular combination of wavelengths of the present invention is considered to be a good classifier in this aspect of the present disclosure when the vectors cluster into the trait groups (elements) found in the training population. For instance, if the training population includes two different elements, a clustering classifier will cluster the population into two groups, with each group uniquely representing either element.

Clustering is described on pages 211-256 of Duda and Hart, Pattern Classification and Scene Analysis, 1973, John Wiley & Sons, Inc., New York. As described in Section 6.7 of Duda, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda. Criterion functions are discussed in Section 6.8 of Duda.

More recently, Duda et al., Pattern Classification, 2nd edition, John Wiley & Sons, Inc. New York, has been published. Pages 537-563 describe clustering in detail. More information on clustering techniques can be found in Kaufman and Rousseeuw, 1990, Finding Groups in Data: An Introduction to Cluster Analysis, Wiley, New York, N.Y.; Everitt, 1993, Cluster analysis (3d ed.), Wiley, New York, N.Y.; and Backer, 1995, Computer-Assisted Reasoning in Cluster Analysis, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

In some embodiments, the pattern recognition platform is based on PCA, as briefly described above. In such an approach, vectors for a selected set of wavelengths can be selected in the same manner described for clustering above. In fact, the set of vectors, where each vector represents spectral data for the select wavelengths from a particular member (e.g. element) of the training populations, can be considered a matrix. In some embodiments, this matrix is represented in a Free-Wilson method of qualitative binary description of monomers (Kubinyi, 1990, 3D QSAR in drug design theory methods and applications, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been accounted for.

Then, each of the vectors (where each vector represents a member of the training population) is plotted. Many different types of plots are possible. In some embodiments, a one-dimensional plot is made. In this one-dimensional plot, the value for the first principal component from each of the wavelengths is plotted. In this form of plot, the expectation is that members of a first group (e.g. a first element within the blood plasma) will cluster in one range of first principal component values and members of a second group (e.g., a second element within the blood plasma) will cluster in a second range of first principal component values.

In one example, the training population comprises two groups: a first element and a second element. The first principal component is computed using the spectral data for the select wavelengths of the present disclosure across the entire training population data set. Then, each member of the training set is plotted as a function of the value for the first principal component. In this example, those members of the training population in which the first principal component is positive are the first element and those members of the training population in which the first principal component is negative are the second element.

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent a first element, a second cluster of members in the two-dimensional plot will represent a second element, and so forth.

In some embodiments, the members of the training population are plotted against more than two principal components and a determination is made as to whether the members of the training population are clustering into groups that each uniquely represents a subgroup found in the training population. In some embodiments, principal component analysis is performed by using the R mva package (Anderson, 1973, Cluster Analysis for applications, Academic Press, New York 1973; Gordon, Classification, Second Edition, Chapman and Hall, C R C, 1999.). Principal component analysis is further described in Duda, Pattern Classification, Second Edition, 2001, John Wiley & Sons, Inc.

Nearest neighbor classifiers are another statistical method on which the pattern recognition platform can be based. Nearest neighbor classifiers are memory-based and require no model to be fit. Given a query point x0, the k training points x(r), r, ..., k closest in distance to x0 are identified and then the point x0 is classified using the k nearest neighbors. Ties can be broken at random. In some embodiments, Euclidean distance in feature space is used to determine distance as:

$$d(i) = \|x(i) - x0\|.$$

Typically, when the nearest neighbor algorithm is used, the expression data used to compute the linear discriminant is standardized to have mean zero and variance 1. In the present disclosure, the members of the training population are randomly divided into a training set and a test set. For example, in one embodiment, two thirds of the members of the training population are placed in the training set and one third of the members of the training population are placed in the test set. Profiles represent the feature space into which members of the test set are plotted. Next, the ability of the training set to correctly characterize the members of the test set is computed. In some embodiments, nearest neighbor computation is performed several times for a set number of wavelengths. In each iteration of the computation, the members of the training population are randomly assigned to the training set and the test set. Then, the quality of the spectral data for the set number of wavelengths is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, Pattern Classification, Second Edition, 2001, John Wiley & Sons, Inc; and Hastie, 2001, The Elements of Statistical Learning, Springer, New York.

The pattern classification and statistical techniques described above are merely examples of the types of models that can be used to construct a model for classification. It is to be understood that any statistical method can be used in accordance with the present disclosure. Moreover, combinations of these described above also can be used. Further detail on other statistical methods and their implementation are described in U.S. patent application Ser. No. 11/134,688, incorporated by reference herein in its entirety.

Computer Implementation

Other embodiments are within the scope and spirit of the invention. For example, due to the nature of software, functions described above can be implemented using software, hardware, firmware, hardwiring, or combinations of any of these. Features implementing functions can also be physically located at various positions, including being distributed such that portions of functions are implemented at different physical locations. Steps of the invention may be performed using dedicated medical imaging hardware, general purpose computers, or both. As one skilled in the art would recognize as necessary or best-suited for performance of the methods of the invention, computer systems or machines of the invention include one or more processors (e.g., a central processing unit (CPU) a graphics processing unit (GPU) or both), a main memory and a static memory, which communicate with each other via a bus. A computer device generally includes memory coupled to a processor and operable via an input/output device.

Exemplary input/output devices include a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory according to the invention can include a machine-readable medium on which is stored one or more sets of instructions (e.g., software), data, or both embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any of the methodologies of the present invention. The term "machine-readable medium" shall accordingly be taken to include, but not be limited to, solid-state memories (e.g., subscriber identity module (SIM) card, secure digital card (SD card), micro SD card, or solid-state drive (SSD)), optical and magnetic media, and any other tangible storage media. Preferably, computer memory is a tangible, non-transitory medium, such as any of the foregoing, and may be operably coupled to a processor by a bus. Methods of the invention include writing data to memory—i.e., physically transforming arrangements of particles in computer memory so that the transformed tangible medium represents the tangible physical objects—e.g., the arterial plaque in a patient's vessel.

As used herein, the word "or" means "and or or", sometimes seen or referred to as "and/or", unless indicated otherwise.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may comprise, for example, singly or in any combination, hard-wired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry. Also, it is intended that operations described herein may be distributed across a plurality of physical devices, such as processing structures at more than one different physical location.

The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Methods of Use

In certain aspects, the present invention is directed to methods of providing information regarding a medium. The method comprises providing a system comprising a light-emitting diode operating at a single wavelength in a deep ultraviolet (UV) range for excitation of a target in a medium and a plurality of semiconductor photodetectors. The system may be configured such that each semiconductor photodetector detects only a subset of emission from the excited target. A medium comprising one or more target analytes may be exposed to at least a single wavelength in the deep UV spectrum from the light-emitting diode of the system to thereby excite the target analyte in the medium. The method may further comprise detecting emission from the excited one or more target analytes via the plurality of semiconductor photodetectors of the system to thereby produce emission data and processing the emission data, thereby providing information regarding the medium.

In certain embodiments, the medium may be selected from the group consisting of a biofluid, water, an aluminum surface, a stainless steel surface, a granite surface, a ceramic surface, a plastic surface, and a metallic surface. In an embodiment, the target analyte may be selected from the group consisting of a microorganism, a biomolecule, and a chemical. In a preferred embodiment, the medium is water and the target analyte is one or more pathogens.

In an embodiment, processing the emission data may comprise identifying presence of one or more target analytes in the medium. Processing the emission data may further comprise identifying the one or more target analytes in the medium. Processing the emission data may further comprise quantifying the one or more target analytes in the medium.

Moreover, certain embodiments of the invention use emission data to determine total microbial load and bioburden measurements. The present invention comprises directing one or more wavelengths of light that are each within a deep ultraviolet (UV) spectrum into a medium comprising a biological substance to thereby excite the biological substance in the medium. Emission is detected from the excited biological substance via one or more semiconductor photodetectors, thereby producing deep UV emission data. The deep UV emission data is analyzed for presence of a deep UV spectral signature indicative of the biological substance, wherein presence of the deep UV spectral signature indicates that the medium comprises a biological substance.

While excitation may be in the deep UV region, emission may be in the UV region, such as in the UVA and UVB regions.

The emission data may be used to determine total microbial load. Microbial load is the number and type of microorganisms contaminating an object or organism, such as non-specific biological and microbiological contamination. Total microbial load indicates the microbiology present in the sample. Emission data may be analyzed for deep UV spectral signatures indicative of microbiology. Emission data may be analyzed for deep UV spectral signatures indicative of presence and quantity of microbiology. For example, analyzing may include comparing the UV spectral signature with a library of UV spectral signatures of varying amounts and types of microbiology on or in a variety of media. Systems of the invention may indicate the total microbial load in the sample after detecting the UV spectral signatures indicative of microbiology.

The emission data may be used to determine bioburden, or the number of bacteria living on a surface or within a liquid. Often, bioburden refers to the number of microorganisms on an unsterilized surface. Emission data may be analyzed for deep UV spectral signatures indicative of presence and quantity of microorganisms. For example, analyzing may include comparing the UV spectral signature with a library of UV spectral signatures of varying amounts and types of microorganisms on or in a variety of media. Systems of the invention may indicate the bioburden in the sample after detecting the UV spectral signatures indicative of the presence or quantity of microorganisms. In certain embodiments, the method may further comprise displaying on a graphical user interface results of the processing step.

In some embodiments, the invention provides different detector and filter configurations for detection using the target thresholds. For example, a first configuration uses a single detector to determine the presence or absence of a target, such as a non-specific contamination. Such a single-detector embodiment may encompass a portable detector, such as a detector used while traveling. Another configuration uses two detectors to determine and distinguish between the presence of microbiology and general biology targets. To specify certain strains of targets in a mixture or sample, a configuration of the invention uses seven detectors. Another configuration uses seven or more detectors to distinguish between dead and live specified strains of targets.

As a non-limiting example, the target may be selected from bacteria, fungi, protein, a cell, a virus, a nucleic acid, a receptor, a ligand, a hormone, a drug, a chemical substance, or any molecule known in the art. For example, the target may be selected from Benzimidazole, 1-Naphthol, Carbofuran, Bisphenol A, Carbaryl-d7, Naphthalene, p-xylene, Tryptophan, Phenanthrene, Tyrosine, ethylestradiol, Propoxur, Ibuprofen, Beta-estradiol, Dimethyl phthalate, Chlopyrifos, Ethylbenzene, Dibutyl phthalate, Benzo[a]pyrene, Benzene, Biphenyl, 3,5,6-Trichloro-2-pyridinol, Bisphenol S, Imidazole, hydrocortisone, Toluene, Alachlor, Atrazine, QB3 Tap water, Di n octyl phthalate, Acetaminophen, Estrone, Glyphosate, Lead, Bis(2-ethylhexyl) phthalate, clarithromycin, Trihalomethane, diisodecylphthalate. phenylalanine, Heptachlor, testosterone, dieldrin, Tozaphenel, Aldrin, DTT, cortisol, and Endrin.

In certain embodiments, the target is a pathogen, or pathogenic bacteria or fungi. A pathogen is a biological agent, such as a microorganism (e.g. bacterium or protozoan), that causes disease or illness to its host. In other embodiments, the target is a gram positive or gram negative bacteria.

Exemplary fungal species include species from the *Candida* genus, *Aspergillus* genus, and *Cryptococcus* genus. In particular embodiments, the specific fungal species include *C. albicans, C. glabarata, C. parapsilosis, C. tropicalis, C. krusei, Cryptococcus neoformans*, and *Cryptococcus gattii*.

Exemplary bacteria include bacteria of the *Escherichia* genus, *Listeria* genus, *Clostridium* genus, Enterobacteriaceae family, *Mycobacterium* genus, *Shigella* genus, *Borrelia* genus, *Campylobacter* genus, *Bacillus* genus, *Salmonella* genus, *Enterococcus* genus, *Streptococcus* genus (such as Pneumococcus), *Acinetobacter* genus, *Strenotrophomonas* genus, *Pseudomonas* genus, *Neisseria* genus, and *Haemophilus* genus, and a combination thereof. The method may also be used to detect the mecA gene, which is a bacterial gene associated with antibiotic resistance.

Pathogen Detection and Identification

The present inventions allow for pathogen detection and identification. Available technologies merely provide an indication of yes or no as to whether there is biological material present. With the present invention, bandpass configuration allows for separation of microbiology from each other and from amino acid signatures. For example, the excitation used in six channel detection can separate out different microbiological strains from each other, as well as from raw amino acid signatures. The ability to separate the bacteria signature without an amino acid is possible due to separation of the channels.

The unique signature associated with three pathogens was used in the invention. By combining known amino acids with pathogen signatures, a configuration was determined for detection at ranges where there are no overlapping parts (FIG. 18). As shown in FIG. 18, when comparing the excitation of Pathogen 1, Pathogen 2, and Pathogen 3, there were overlapping regions and non-overlapping regions. For example, the overlapping regions were observed at particular excitations. The non-overlapping regions indicated the unique signature for each pathogen. By using separate channels within the deep UV range, emission may be detected that differentiates bacteria and other pathogens from one another, thereby allowing for identification of the bacteria. If the signals could not be separated, the bacteria and other pathogens could not be distinguished and there would only be an indication of whether or not a biological substance was present in the sample.

Figure 31:
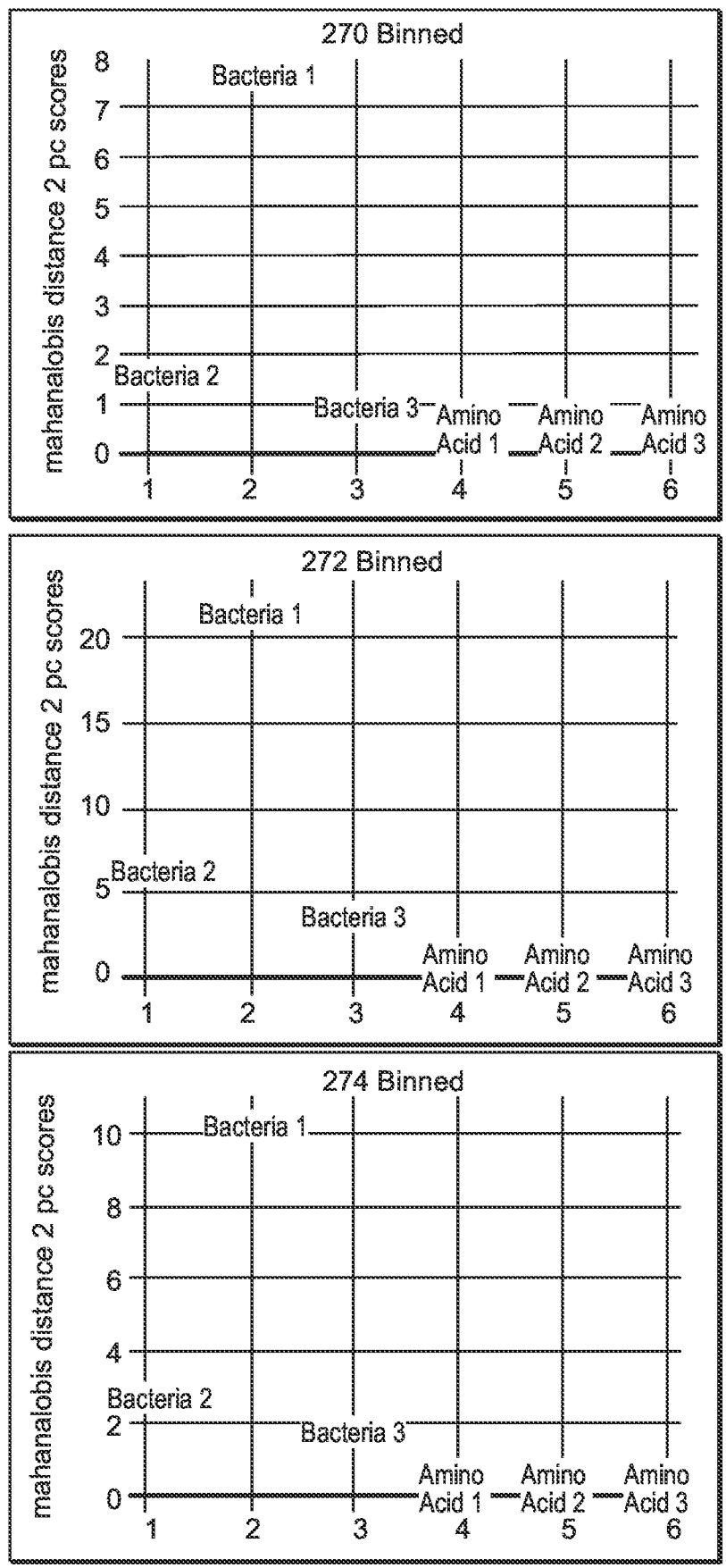
FIG. 31 shows the Mahalanobis Distance plots of emission-excitation matrix (EEM) spectra for bacterial and amino acid signatures.

To separate the microbiology targets, Mahalanobis Distance (see FIG. 31) was implemented using the bacterial and amino acid signatures emission-excitation matrix (EEM) spectra. The bacterial signatures and amino acid signatures are shown in FIG. 31. The EEM signatures were normalized and binned into six channels. The Mahalanobis Distance analysis looked for the largest difference between the bacterial and amino acids. The wavelengths indicated separated the microbiology from the amino acid signatures.

As an example, the present invention may be used to test for presence of *Staphylococcus Aureus* in tap water. A user may input a source of the medium being tested, e.g. tap water. The sample (e.g. tap water) would then be scanned by the apparatus of the present invention. Results would be processed by comparing the spectra from the scanned tap water sample to a database of known spectra from known sources. If the spectrum for the sample is within the threshold for a known source, then the medium quality (e.g. the water quality of the tap water) is output. However, if the sample is not within the threshold, then the spectrum for the sample is compared to a database of contaminants. For example, the database of contaminants includes lab-produced samples of varying concentrations for various bacterial and chemical components within various sources.

If the spectrum for the sample is within a threshold for a contamination source from the contaminant database, then the contamination may be identified. For instance, the tap water sample may match up with a database entry of a known bacterial contamination, e.g. *Staphylococcus Aureus*. The tap water sample would then be identified as having a contaminant which is *Staphylococcus Aureus*.

The contamination may be further quantified based on calculations from concentration studies of the contaminants. For example, the concentration of *Staphylococcus Aureus* in the tap water sample would be determined based on concentration studies of *Staphylococcus Aureus* in samples from tap water. The results of the scan in the tap water example would indicate the presence of *Staphylococcus Aureus* as a contaminant and the concentration of *Staphylococcus Aureus* in the tap water sample.

Water Analysis

The systems and methods of the invention are applicable to many different types of media and surfaces, as already mentioned throughout this application. A particular area of interest is water analysis and water quality. In that manner, the present invention provides a range of targets that can be detected within different water sources and water types, such as tap, bottle, and well water and on aluminum and stainless steel surfaces. Target contaminants may be selected from the group consisting of pathogens, amino acids, hormones, industrial chemicals, pharmaceuticals, and biomarkers. In an embodiment, urine and saliva matrices may be analyzed for the human biomarker analysis. In certain embodiments, for a deeper water analysis, users may request a collection kit and EPA certified facilities will email them a full, easy to understand, report. Quantification according to the present invention may positively impact the creation of cleaner rivers and water sources.

For example, devices of the invention may be used for monitoring and detection of water quality in industrial and manufacturing processes. Devices of the invention may be used for water quality detection in water kiosks that provide sale of tap water, such as in developing countries. Utilities providers may use devices of the invention to ensure water quality being provided to customers. Similarly, building owners may use devices of the invention for monitoring and detection of water quality within a building, such as to ensure safe water for tenants. Devices of the invention may also be used in the food and beverage industry, pharmaceutical industry, and healthcare industry.

Figure 25:
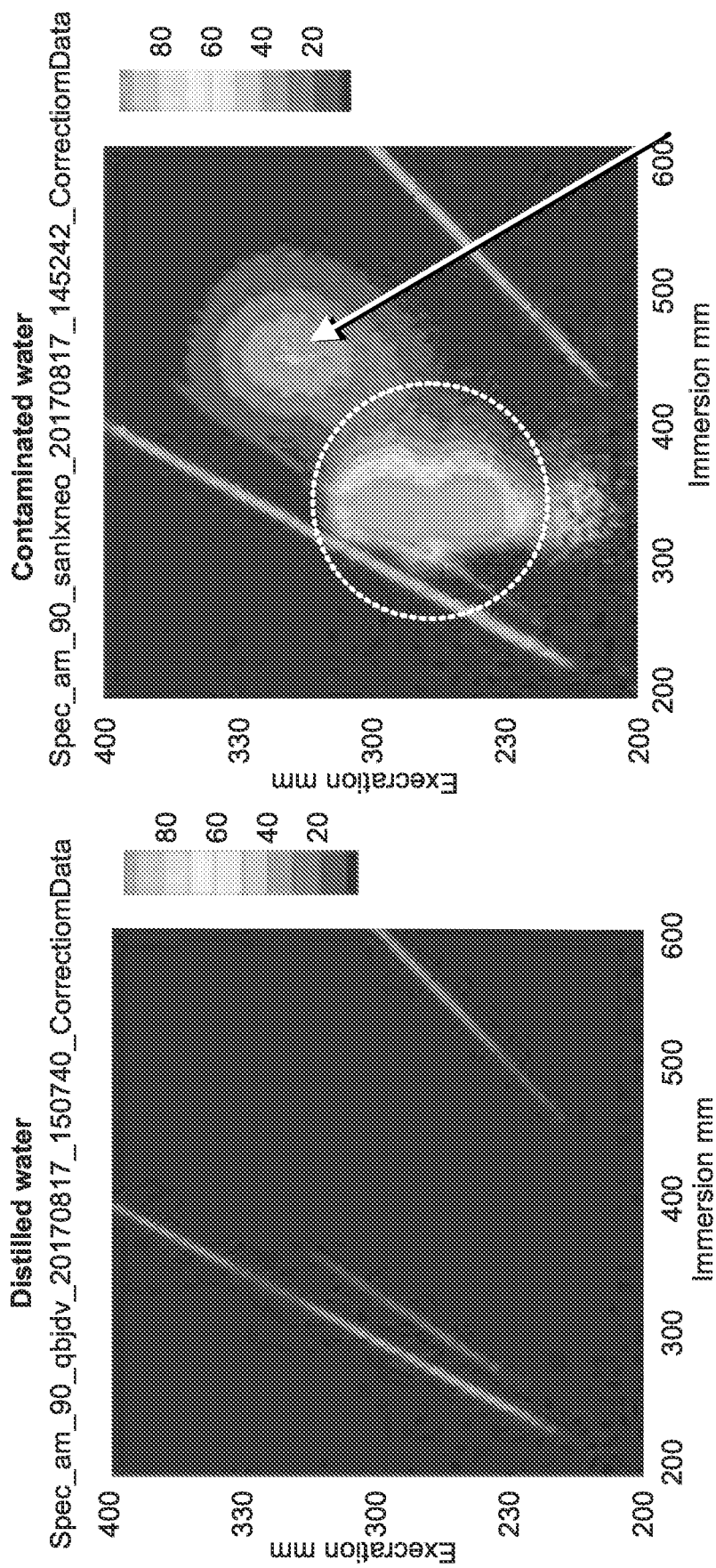
FIG. 25 shows EEM for tap water and pure water.
Figure 26:
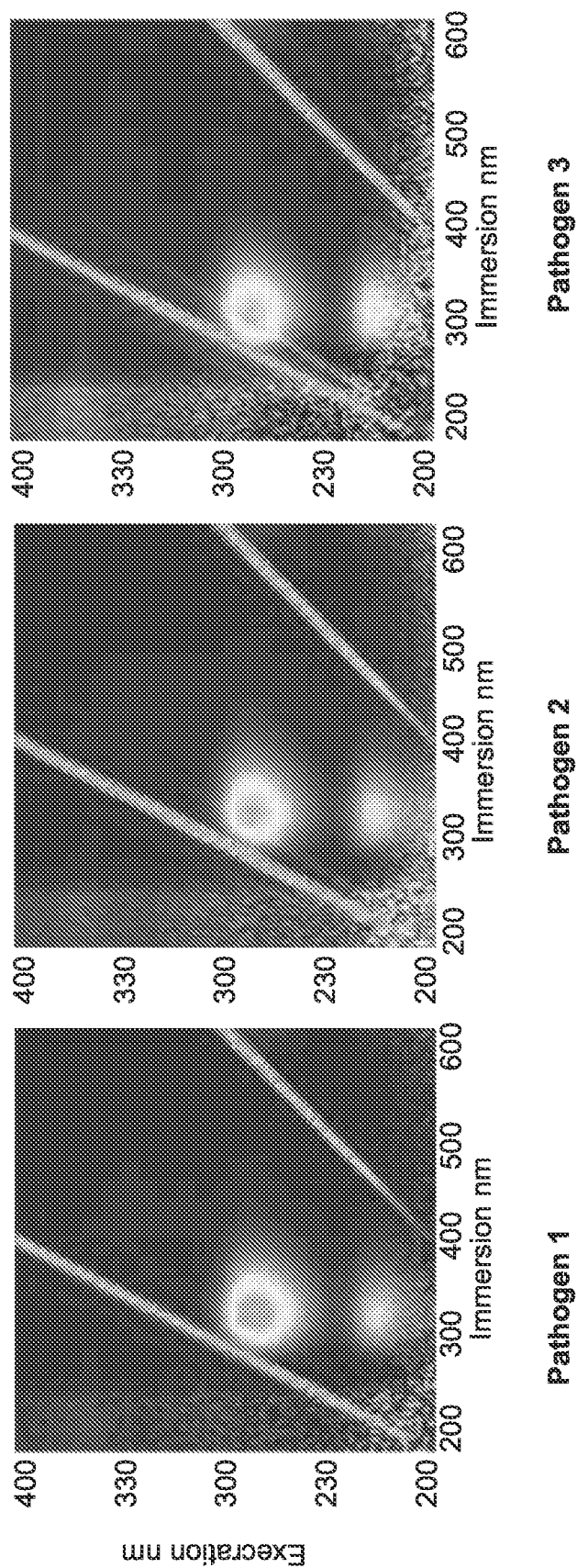
FIG. 26 shows bacteria spectral signatures in tap water.

There is bacterial contamination in tap water. If the water was pure water, no fluorescence would show when doing an EEM (FIG. 25). Tap water has a residual signature in region that is linked to decomposing biological substances. However, pathogens such as bacteria and various other targets fluorescence in the region marked by the circle (FIG. 26).

For example, the present invention may be used to test water quality. A user may input a source of the water being tested, e.g. bottled water, tap water from a particular location, or well water. The water sample (e.g. bottled water) would then be scanned by the apparatus of the present invention. Results would be processed by comparing the spectra from the scanned water sample to a database of known spectra from known sources. If the spectrum for the sample is within the threshold for a known source, then the water quality is output. However, if the sample is not within the threshold, then the spectrum for the sample is compared to a database of contaminants. For example, the database of contaminants includes lab-produced samples of varying concentrations for various bacterial and chemical components within various sources.

If the spectrum for the sample is within a threshold for a contamination source from the contaminant database, then the contamination may be identified. For instance, the bottled water sample may match up with a database entry of a known *E. coli* contamination in bottled water. The water sample would then be identified as having a contaminant which is *E. coli*.

The contamination may be further quantified based on calculations from concentration studies of the contaminants. For example, the concentration of *E. coli* in the water bottle sample would be determined based on concentration studies of *E. coli* in water samples from water bottles. The results of the scan in the water bottle example would indicate the presence of *E. coli* as a contaminant and the concentration of *E. coli* in the water bottle sample.

Food

The present invention may help to shift global agricultural land to being more than 1% certified organic. By using detection of the present invention, safe and environmental practices may flourish. Awareness may drive markets to efficiency and innovation, and new markets may be created for other technologies.

In an example, in consumer signaling, consumers may be empowered by molecular insight into their food and water. The consumer interest may incentivize retailers to invest in detection technology for the present invention. Retailers may drive adoption throughout the food and water supply chain such as through the distributor, processor/supplier, or grower/water source.

In an embodiment, the spectral database of the present invention may be valuable to retailers wanting to gain customer confidence. In an embodiment, the present invention may become the standard in molecular scanning. In an embodiment, the present invention may create store-specific scanning technology. In an embodiment, a database according to the present invention may be accessed for a monthly or yearly fee. In an embodiment, the present invention may monetize throughout the supply chain on the back of consumer knowledge and demand for cleaner products. Retail stores may rely on such a clean supply chain reputation and may be incentivized to integrate the present invention in stores and throughout suppliers.

Figure 27:
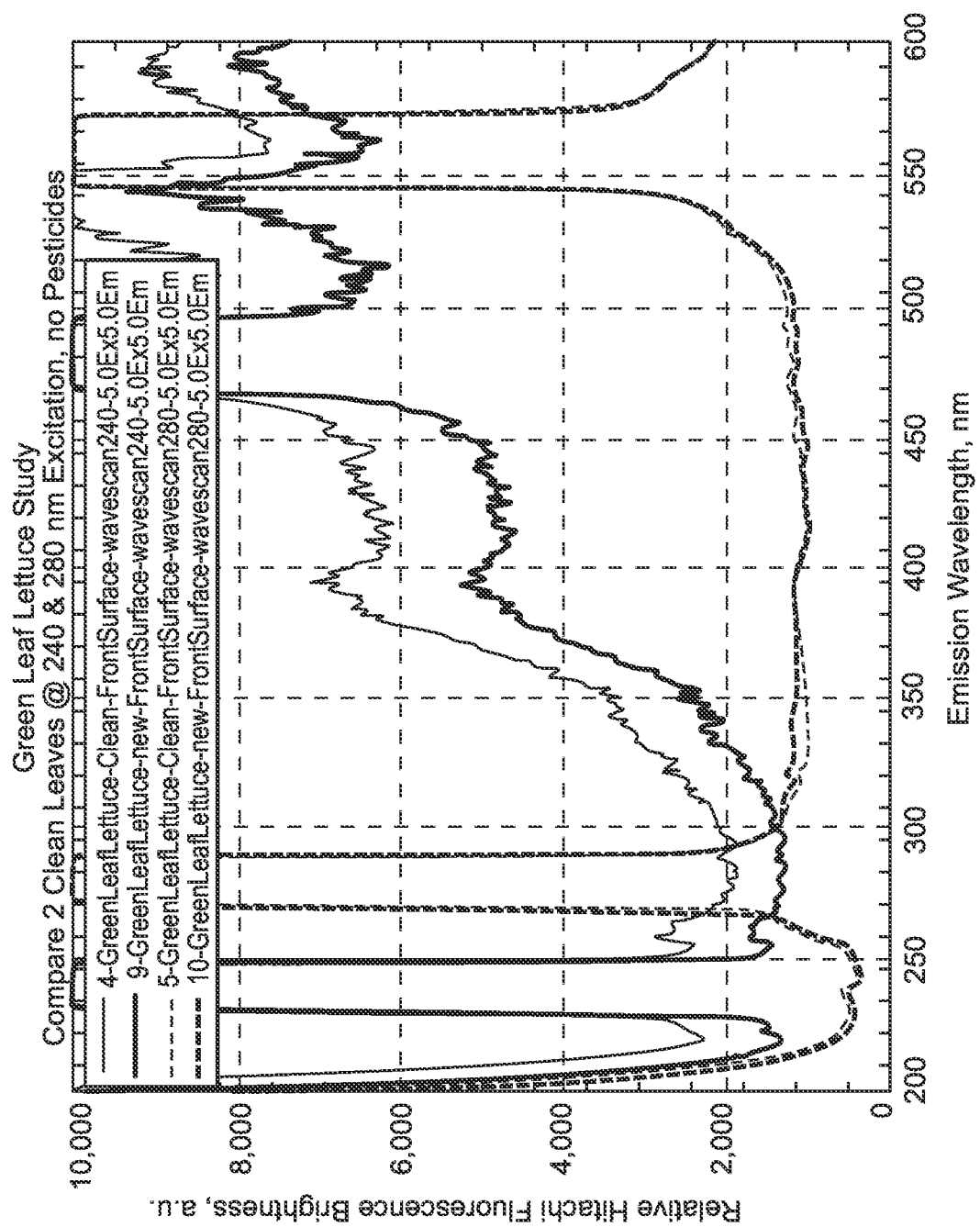
FIG. 27 shows fruit and vegetable pesticide scans.
Figure 27:
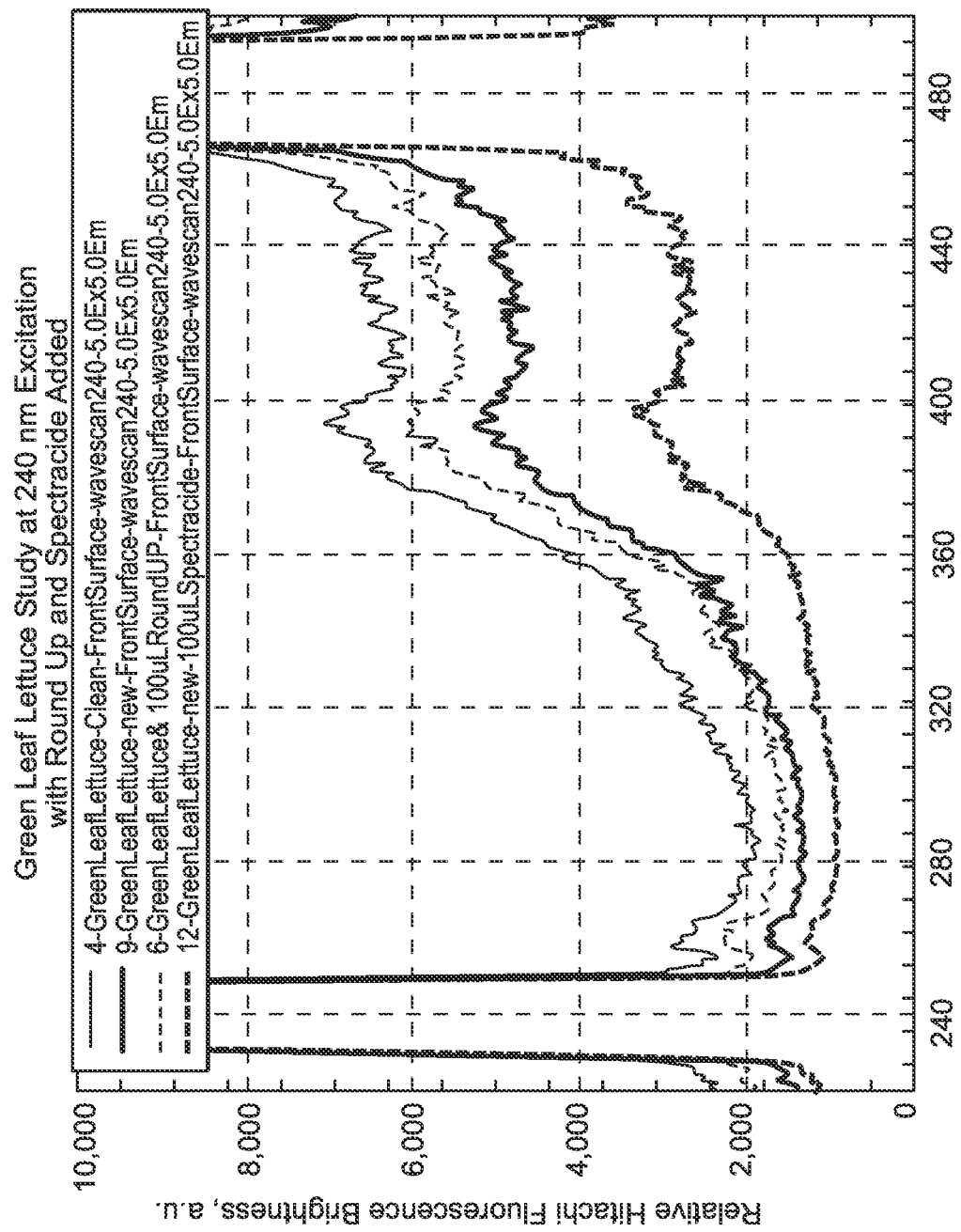
Figure 27:
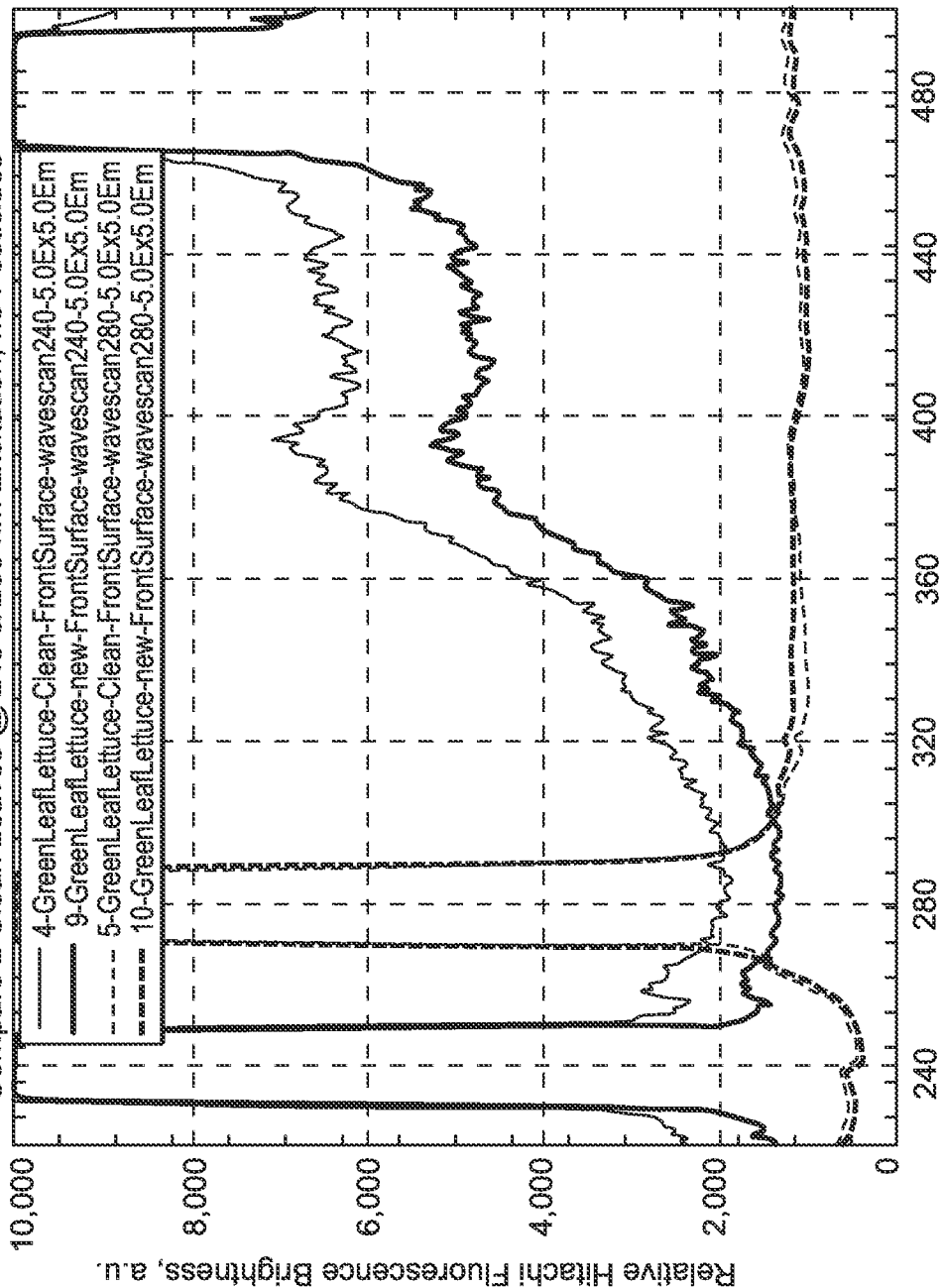
Figure 27:
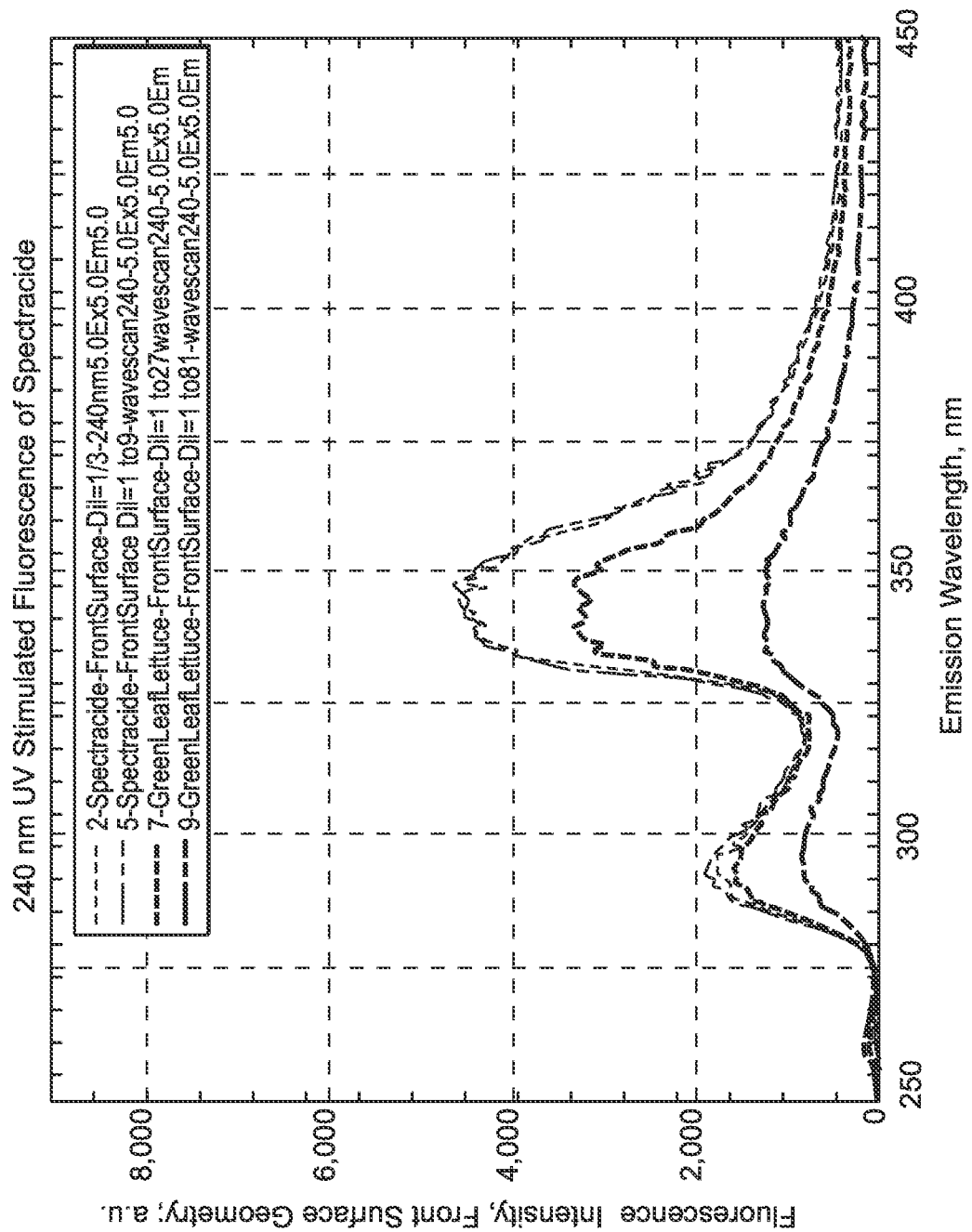

Fruit and vegetable pesticide scans are shown in FIG. 27.

For example, the present invention may be used to test for presence of a pesticide on a fruit or vegetable. A user may input a source of the medium being tested, e.g. a fruit or vegetable. The sample (e.g. an apple) would then be scanned by the apparatus of the present invention. Results would be processed by comparing the spectra from the scanned apple sample to a database of known spectra from known sources. If the spectrum for the sample is within the threshold for a known source, then the medium quality is output. However, if the sample is not within the threshold, then the spectrum for the sample is compared to a database of contaminants. For example, the database of contaminants includes lab-produced samples of varying concentrations for various bacterial and chemical components within various sources.

If the spectrum for the sample is within a threshold for a contamination source from the contaminant database, then the contamination may be identified. For instance, the apple sample may match up with a database entry of a known pesticide contamination, e.g. flazasulfuron. The apple sample would then be identified as having a contaminant which is flazasulfuron.

The contamination may be further quantified based on calculations from concentration studies of the contaminants. For example, the concentration of flazasulfuron in the apple sample would be determined based on concentration studies of flazasulfuron in similar samples from apples. The results of the scan in the apple example would indicate the presence of flazasulfuron as a contaminant and the concentration of flazasulfuron in the apple sample.

Embodiments of the invention may be used to detect contaminants on foods. As an example, the invention may be used to detect pesticides on fruits and vegetables. For example, the invention may be used to detect a pesticide on a kale leaf. As an example, the invention may be used to detect a bacterial increase on the surface of meats and fish to determine freshness or lack thereof.

In an embodiment, the invention may be used to monitor the process wash water quality for fresh produce cleaning, such as that completed by food producers and suppliers, can give early indications of contamination events. For instance, tested sources may include well water directly from a tank, well water at tap, a first wash with biocide, direct runoff from produce, waste water at the end of a process line, or water from plastic crate wash. As another example, the invention can be used by individuals who wash a head of romaine lettuce and then scan the captured water to get an indication of sanity level or safety level of the romaine lettuce.

Healthcare

The present invention may help to reduce hospital-acquired infections. Each year, 1.7 million patients are infected by hospitals. A staggering 1 in 25 patients resulted in approximately 99,000 deaths unrelated to conditions for which the patients were admitted to the hospitals. Hospital-acquired infections in the United States result in $38 billion in extra costs each year. This needless contamination may be due to unsterilized surfaces in the hospitals. With the present invention, target analytes may be detected on surfaces such as stainless steel and aluminum. These surfaces are prevalent in hospital settings.

For example, the present invention may be used to test for presence of *Staphylococcus Aureus* on surfaces in a hospital. A user may input a source of the medium being tested, e.g. an aluminum surface. The sample (e.g. an aluminum surface) would then be scanned by the apparatus of the present invention. Results would be processed by comparing the spectra from the scanned aluminum surface sample to a database of known spectra from known sources. If the spectrum for the sample is within the threshold for a known source, then the medium quality is output. However, if the sample is not within the threshold, then the spectrum for the sample is compared to a database of contaminants. For example, the database of contaminants includes lab-produced samples of varying concentrations for various bacterial and chemical components within various sources.

If the spectrum for the sample is within a threshold for a contamination source from the contaminant database, then the contamination may be identified. For instance, the aluminum surface sample may match up with a database entry of a known bacterial contamination, e.g. *Staphylococcus Aureus*. The aluminum surface sample would then be identified as having a contaminant which is *Staphylococcus Aureus*.

The contamination may be further quantified based on calculations from concentration studies of the contaminants. For example, the concentration of *Staphylococcus Aureus* in the aluminum surface sample would be determined based on concentration studies of *Staphylococcus Aureus* in samples from aluminum surfaces. The results of the scan in the aluminum surface example would indicate the presence of *Staphylococcus Aureus* as a contaminant and the concentration of *Staphylococcus Aureus* in the aluminum surface sample.

Blockchain

In certain embodiments, blockchain technology may be used. Blockchain is a digital, decentralized transaction and data management technology, such as described in Yli-Huumo et al, Where Is Current Research on Blockchain Technology?—A Systematic Review, PLOS ONE, 2016, incorporated herein. Data integrity and authentication are essential issues in the Blockchain environment. It is necessary that when data gets sent and verified, it has not been altered or tampered with. A private key may be an authentication element. A smart phone may be used as a second authentication factor. By using blockchain in the present invention, sample data may be shared with the database and tampering of that sample data may be avoided.

Figure 28:
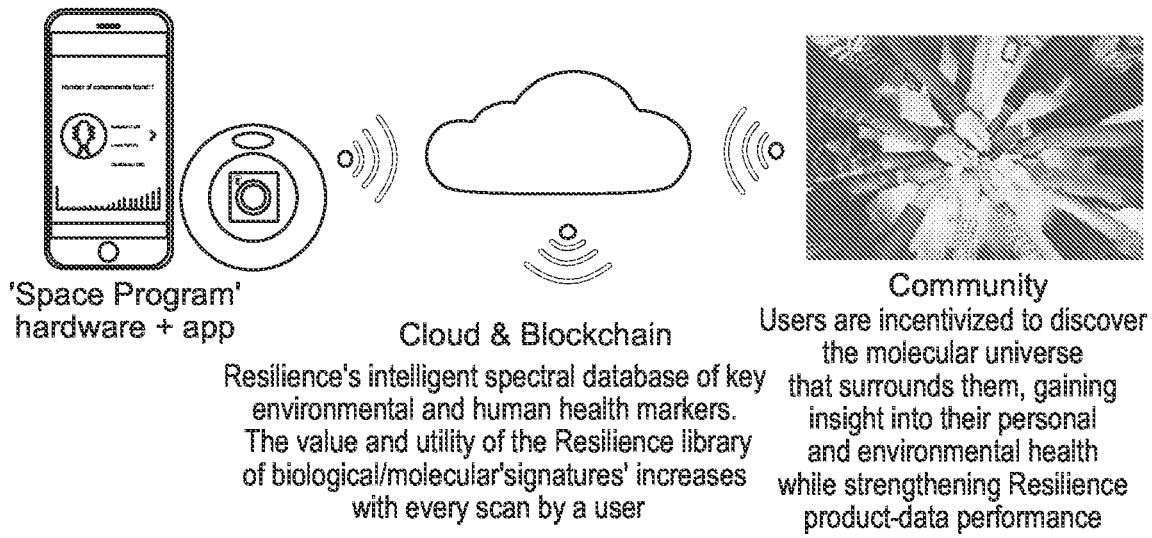
FIG. 28 shows the ecosystem and communication between users, the cloud and blockchain, and the detector and processor.

The use of blockchain may be directed to quantified water, quantified food & agriculture, quantified environment, and quantified health-home diagnostics. In the ecosystem according to the present invention, product, data, and people interact (FIG. 28). Further, cloud and blockchain provide an intelligent spectral database of key environmental and human health markers. The value and utility of the library of biological/molecular 'signatures' increases with every scan by a user. The community of consumers is also important, as users are incentivized to discover the molecular universe that surrounds them. These consumers allow for gaining of insight into their personal and environmental health while strengthening the product-data performance of the present invention.

Figure 29:
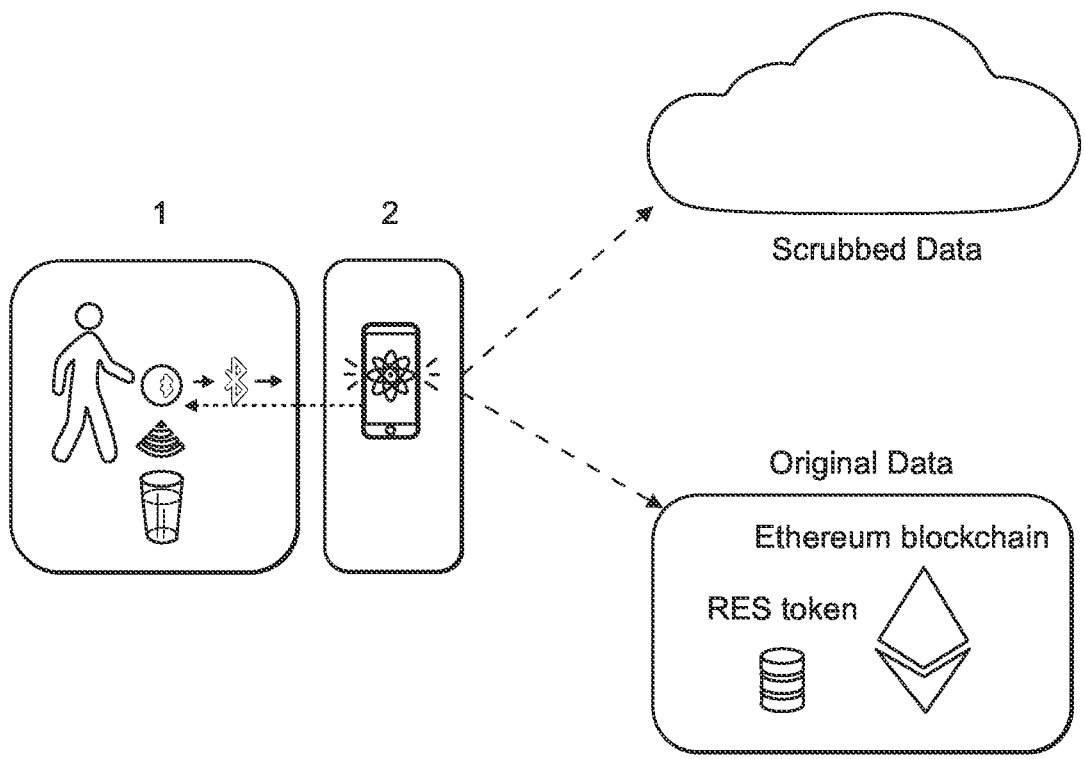
FIG. 29 shows how data is secured on an embodiment using blockchain.

In certain embodiments, data may be secured on the blockchain, which may be the first global intelligent database of key environmental and human health markers (FIG. 29). Users may choose what gets written to the blockchain (using a RES token). Scanned data is private and hashed by default. Data is immutable and cannot be erased or altered by anyone. To view data a "View key" is needed that only the user will have. All data may be geotagged and time-stamped. Users may earn RES tokens on data if written to the blockchain and made available for analysis (pending SEC rules).

Figure 30:
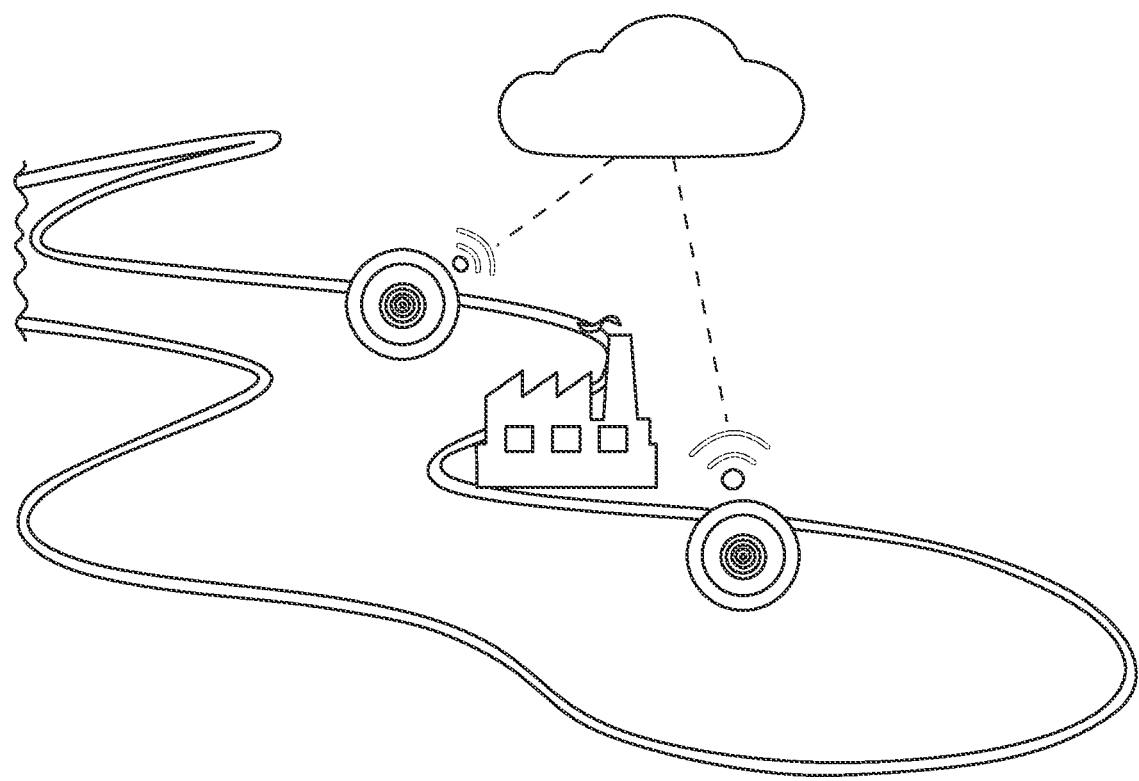
FIG. 30 shows monitoring devices upstream and downstream of a polluter.

In an embodiment, time-stamped, geo-tagged, and encrypted data may be written to the blockchain. Monitoring devices according to the present invention may be stationed before and after point-source polluters (FIG. 30). This will establish a guardian network of real-time, verified data that cannot be manipulated or deleted.

In an embodiment, consumers may scan whole foods for contaminants. Consumers may scan bio-fluids for health markers. In an embodiment, government agencies may monitor public waterways. In an embodiment, supermarkets may monitor growers and suppliers. In an embodiment, food and beverage processors may scan water and surfaces. In an embodiment, hospitals may scan facilities.

Atmospheric Conditions

In particular embodiments, the present invention may be used in different atmospheric conditions. Preferably the invention is used under Earth's atmospheric conditions. The invention may be used under other atmospheric conditions. As non-limiting examples, the present invention may be used for detection of target analytes in media on a space station, a rocket, on Mars, or under water.

Detection of Gram+/Gram−

Figure 32:
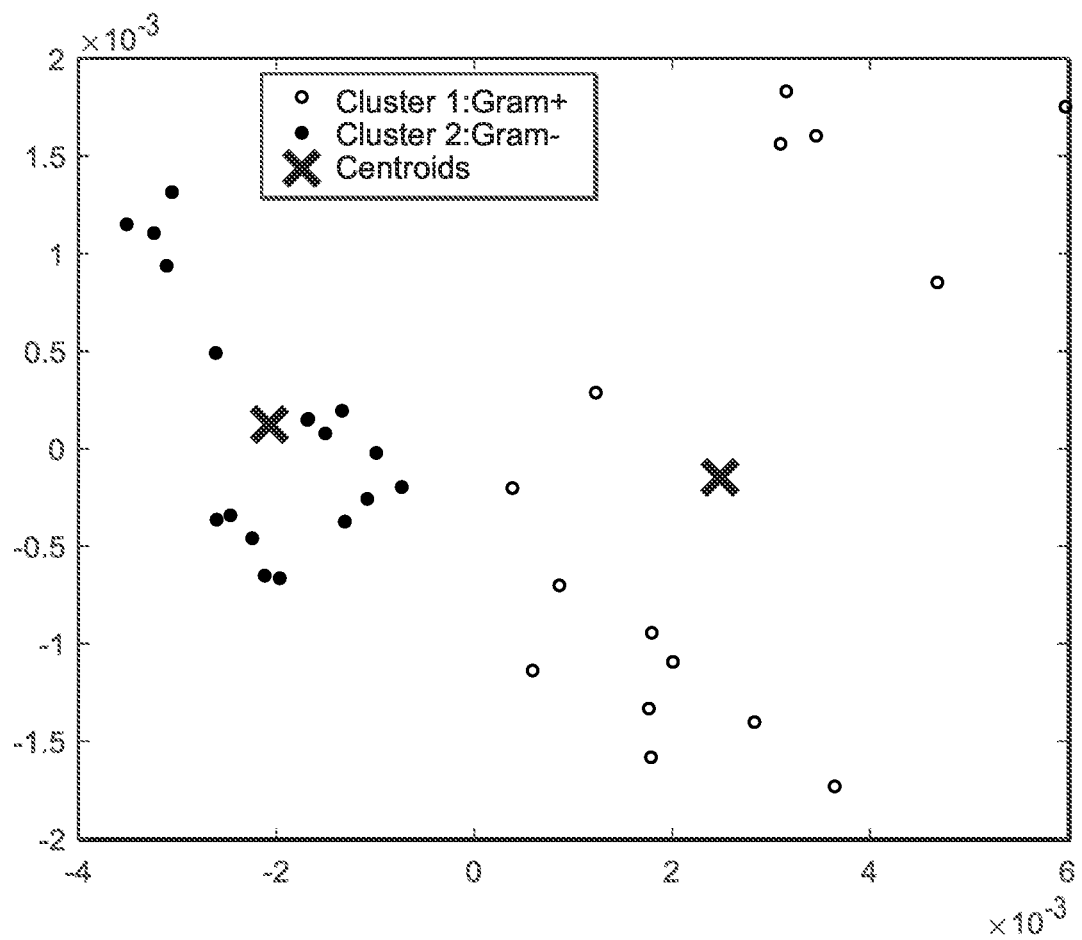
FIG. 32 shows clustering of spectra of gram+ and gram− bacteria species.

In certain embodiments, the invention is used to tell the difference between Gram/+ and Gram/− bacteria. In a non-limiting study, the invention was used on six bacteria strains. The gram+ and gram− bacteria species used in a non-limiting study include *Listeria welshimeri, Listeria seeligeri, Staphylococcus epidermidis, Klebsiella aerogenes, Pseudomonas putida, Enterobacter,* and *Escherichia coli*. FIG. 32 shows the clustering of spectra of the gram+ and gram− bacteria species.

EXAMPLES

Example 1

FIG. 1 shows the scanner or detector according to the present invention. The device is small and portable. The device includes an indicator, which may be an OLED display. The device also includes the lens and detectors, as well as a scan button. Optionally, there may be a micro grip texture on the device.

Example 2

Figure 2:
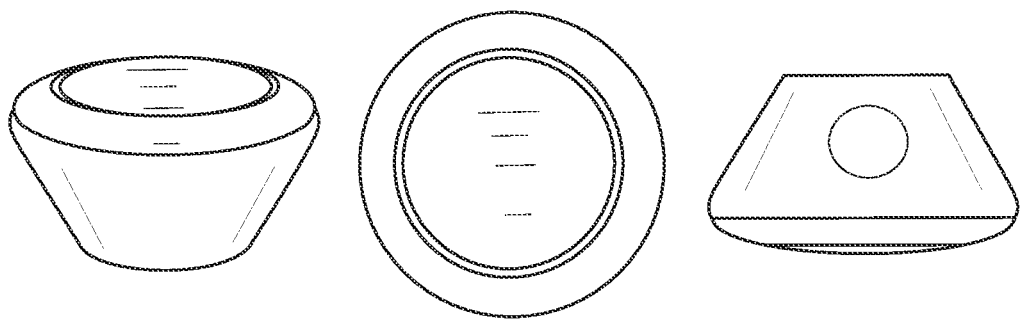
FIG. 2 shows side and top views of the OLED display scanner or detector according to the present application.

FIG. 2 shows side and top views of the OLED display scanner or detector according to the present application. The display may be an E-ink display in certain embodiments. The display screen may be the user interface for the device, with all components of the system included in the detector device. The device is small and portable. The device is also user-friendly, as evidenced by the simple scanning button located on a side of the device.

Example 3

Figure 3:
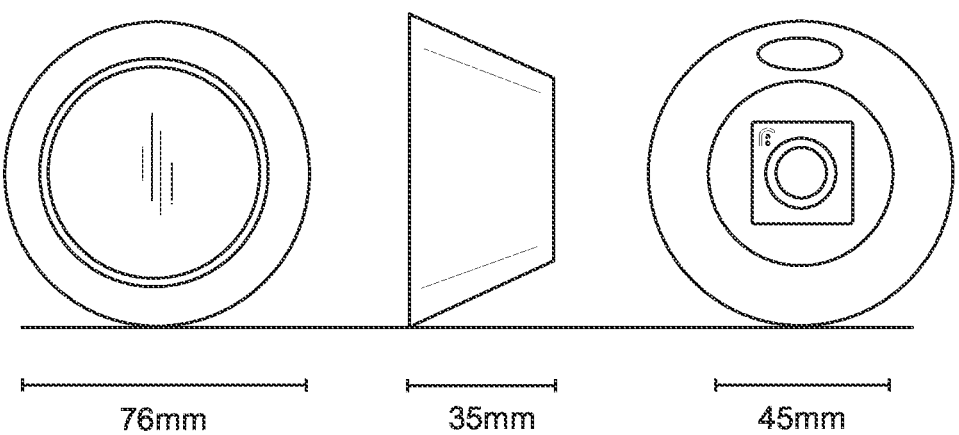
FIG. 3 shows the dimensions of the scanner or detector.

FIG. 3 shows the dimensions of the scanner or detector. The top of the device, or the display screen, may measure 76 mm in diameter. The scanning side of the device, or the side containing the detector and lens, may measure 45 mm in diameter. The device may have a thickness of 35 mm.

Example 4

Figure 4:
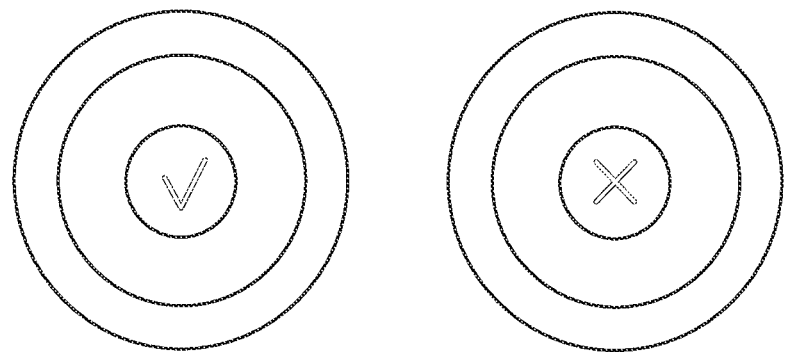
FIG. 4 shows the display for results of the sample.

FIG. 4 shows the display for results of the sample. The display screen may have simple, easy-to-read features. For example, a check may mean that the sample is cleared, while an X may mean that the sample is contaminated.

Example 5

Figure 5:
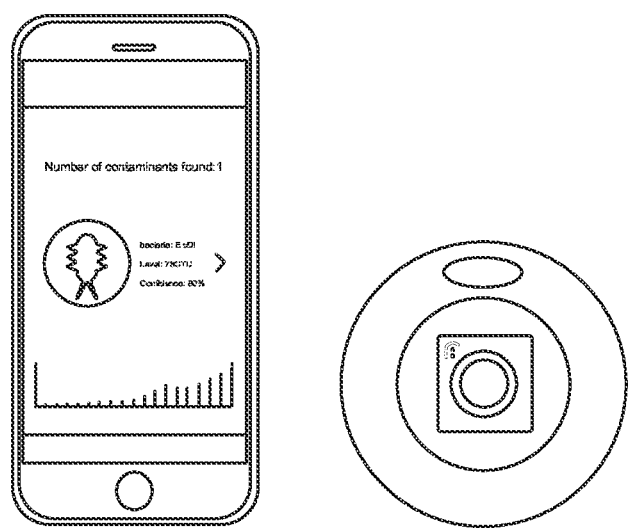
FIG. 5 shows the user interface on an external source such as a smartphone.

FIG. 5 shows the user interface on an external source. The user interface may be on a smartphone. Such an embodiment differs from having the user interface integrated in the detector device itself. The user interface may also be on other suitable means, such as an external laptop computer or tablet.

Example 6

Figure 6:
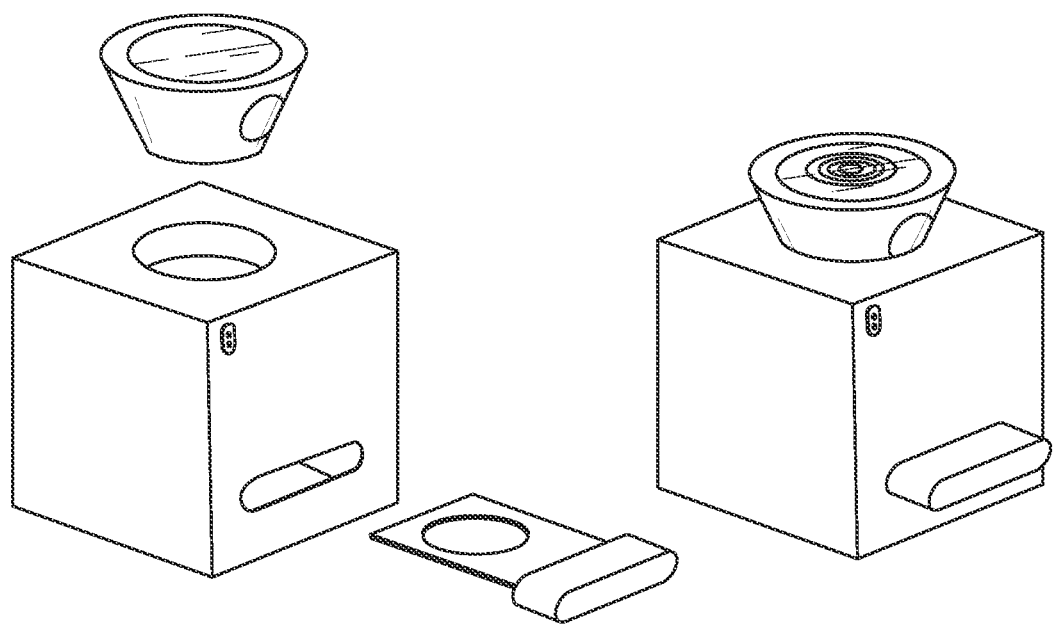
FIG. 6 shows a minilab embodiment of the present invention.
Figure 7:
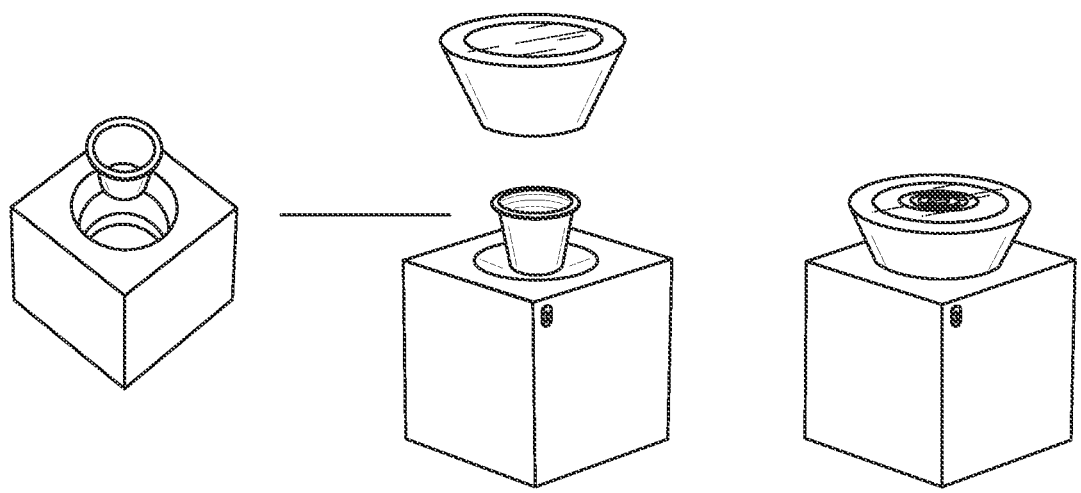
FIG. 7 shows a minilab embodiment of the present invention

In certain embodiments, the detector of the present invention may be used in a minilab setup. As shown in FIG. 6, the minilab may have a housing, a detector, and a sample slide plate. As shown in FIG. 7, the minilab may have a housing, a detector, and a sample cup. The sample may be placed on the sample slide plate or sample cup and then inserted into the minilab housing. The detector may be fitted within the housing to stabilize the detector while scanning.

Example 7

Figure 8:
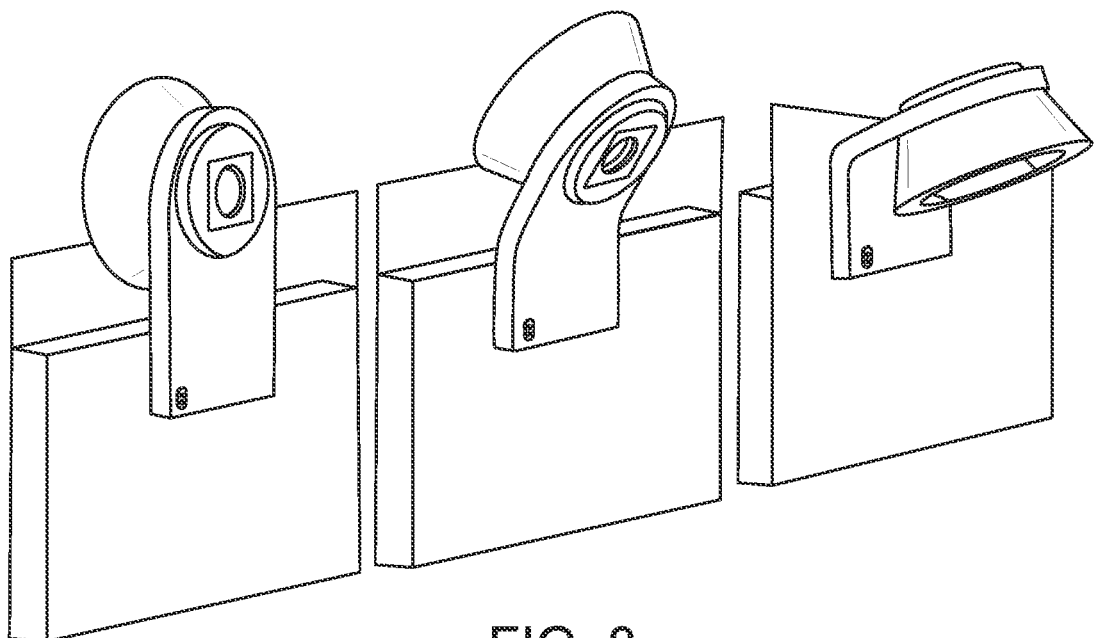
FIG. 8 shows wedge embodiments of the present invention.

In certain embodiments, the detector of the present invention may be used in a wedge setup. As shown in FIG. 8, the wedge may come in different angles to fit any surface. The wedge may use cases (sink, toilet, shelf, wall). The back side of the wedge may include a VHB tape layer to strongly stick to any type of surface.

Example 8

Figure 9:
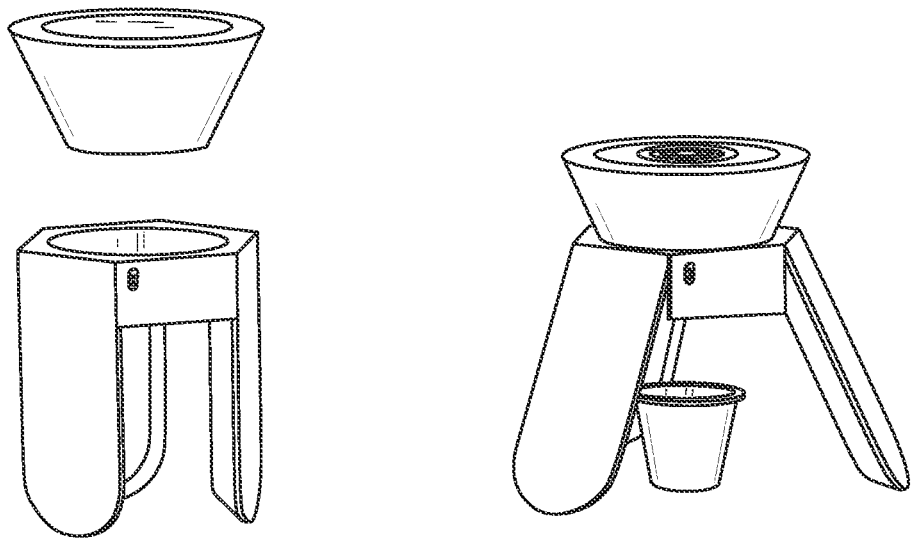
FIG. 9 shows an embodiment using a small sample cup.
Figure 10:
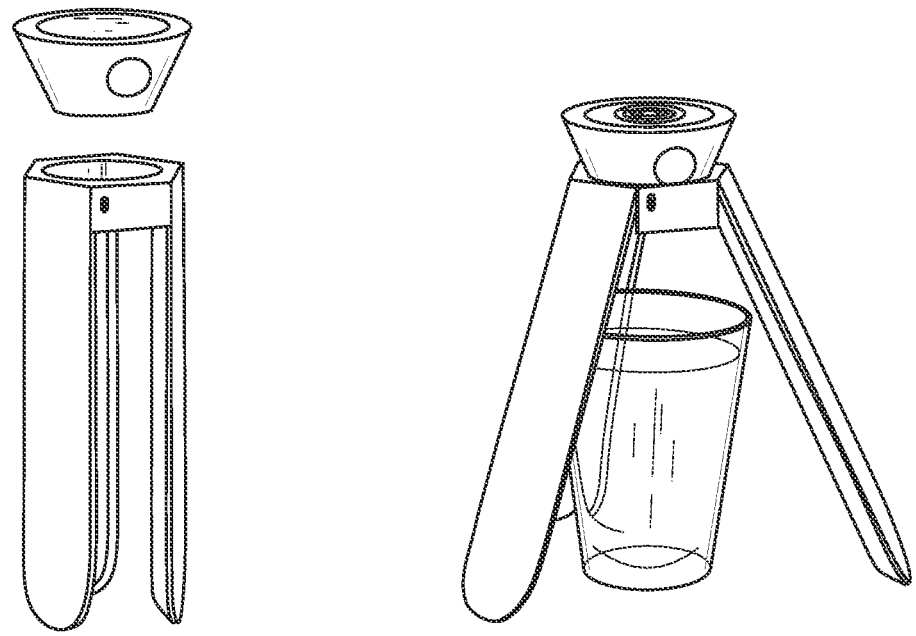
FIG. 10 shows an embodiment using a large sample.

In certain embodiments, systems of the invention comprise a housing that has multiple components, and one of the components is a base or tripod. In such an embodiment, the detector of the present invention may be used in a tripod setup. As shown in FIG. 9, the detector may be used for detection of a sample in a small sample cup. As shown in FIG. 10, the detector may be used to for detection of a large sample. The tripod setup allows for the detector to be stabilized while scanning.

Example 9

Figure 11:
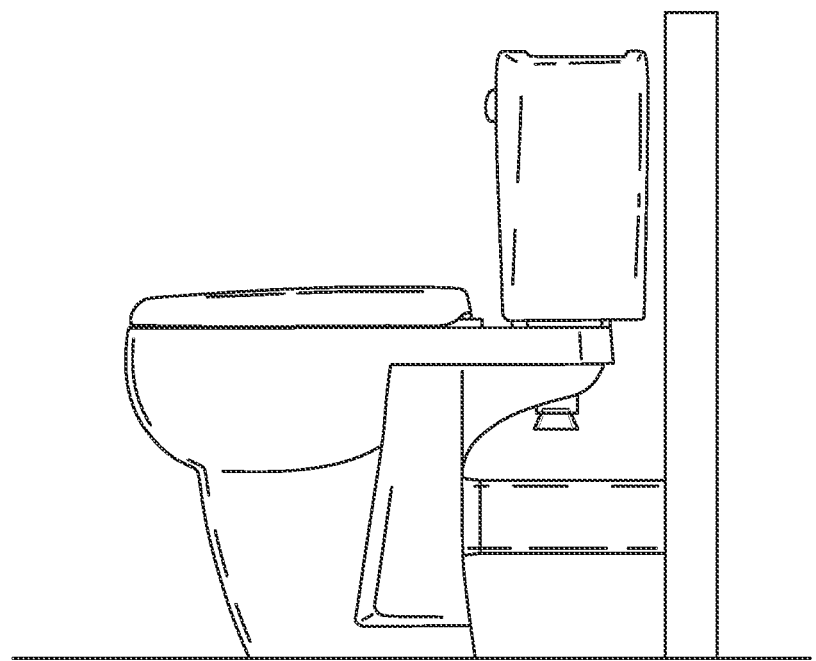
FIG. 11 shows an embodiment using the detector as a toilet adapter.

As shown in FIG. 11, the detector may be used as a toilet adapter. The toilet adapter system may be used to analyze urine within the toilet bowl water. For example, the adapter may detect anomalies or diseases within the urine. Measurements may include high protein content and urinary tract infections (UTI). In addition, the device may be used as an early warning system for diseases and health markers. For example, the device may be used for disease detection, as certain cancers may shift the spectral signature of urine in the UV region. As another example, the device may be used to detect hormones from ovulation cycles and pregnancy markers, such as hCG. Users may be notified of the detection results by smartphone notification.

Example 10

Figure 12:
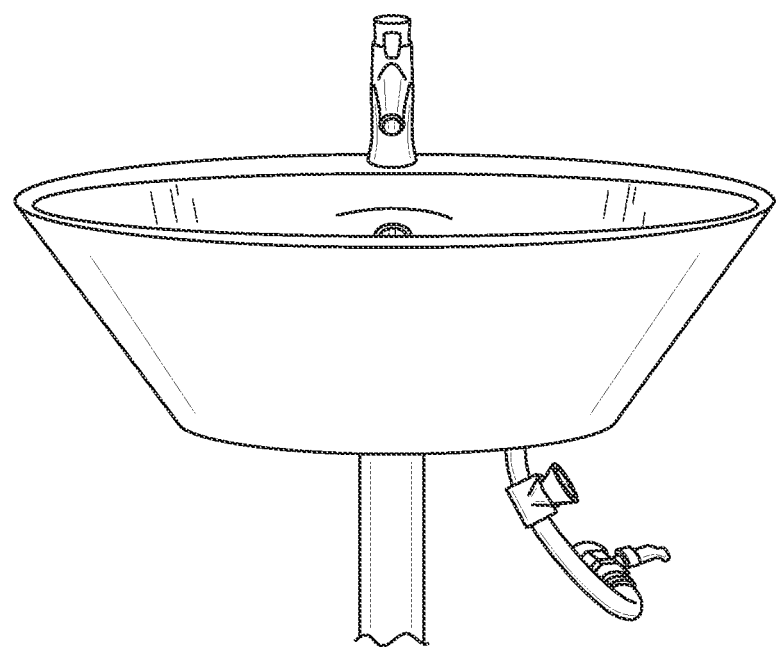
FIG. 12 shows an embodiment using the detector using as a sink adapter.

As shown in FIG. 12, the detector may be used a sink adapter. This allows users access to the water quality within their environment, such as in a home, hospital setting, or work environment. People use sinks frequently throughout the day. If a contaminant is present in the water source for the sink, there may be increased safety concerns. By installing the detector on the plumbing leading to the faucet of a sink, users have the opportunity to detect the water source before using the water in the sink. Further, users may opt to obtain sample data more frequently or set the detector to scan the water source at specified time periods to monitor the water quality.

Example 11

Figure 13:
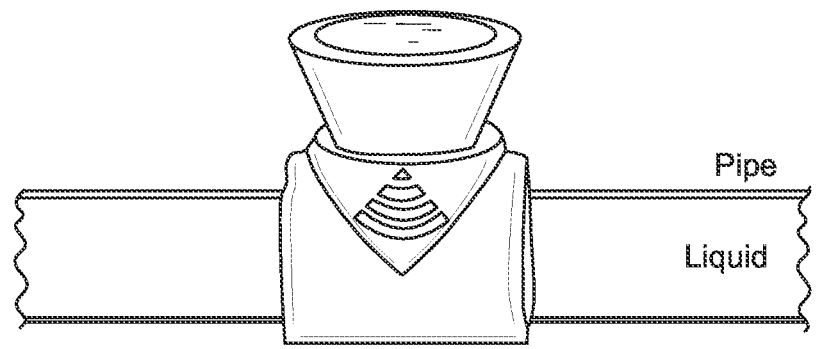
FIG. 13 shows an embodiment of an on-line detector.

FIG. 13 shows an embodiment of an on-line detector. In the on-line embodiment, the detector is coupled to a water source, such as a pipe. In some cases, the detector is mounted to a pipe attachment, such as a 2 inch pipe attachment or a T-junction pipe fitting. The device provides detection of the liquid inside the pipe. In some examples, similar to Example 10, the device is coupled to a pipe for a sink and detects bioburden or total microbial load in the liquid leading to the faucet of the sink. The on-line embodiment provides a low profile with a detection window for non-disruption mounting and un-mounting of the device.

Example 12

Figure 14:
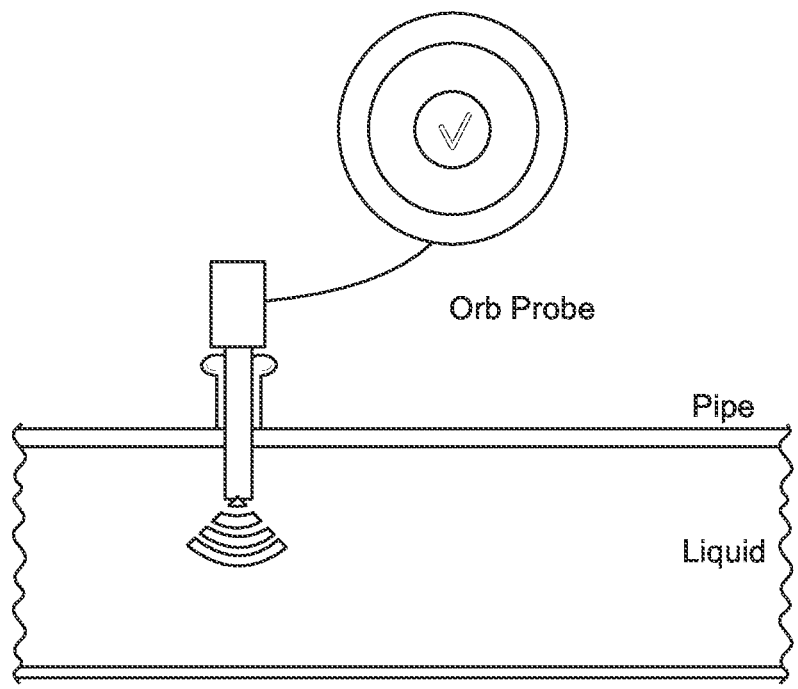
FIG. 14 shows an embodiment of an in-line detector probe.

FIG. 14 shows an embodiment of an in-line detector probe. As shown in FIG. 14, the probe is inserted into the pipe, with part of the probe disposed within the pipe, for detection of bioburden or total microbial load in the liquid flowing through the pipe. In some examples, the probe may be used in industrial settings to monitor water quality, particularly where a sink or end-point to a line is unavailable or if water quality should be monitored in a particular closed section of a manufacturing process.

Example 13

Figure 15:
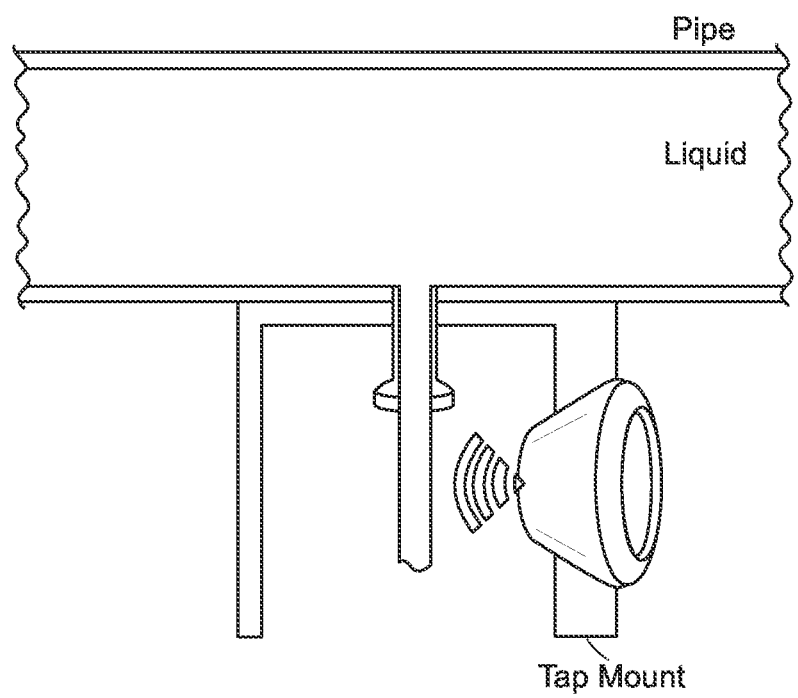
FIG. 15 shows an embodiment of an off-line stand-off detector.

FIG. 15 shows an embodiment of an off-line, stand-off detector, such as a tap attachment. The device monitors water quality from a tap mount on the line, but the device itself is off-line, or off of the pipe. Providing the device off-line as a stand-off detector eliminates detector biofouling and allows high accuracy sample readings.

Example 14

The invention uses deep UV autofluorescence to detect and identify various strains of bacteria. Bacteria cells have unique autofluorescence signatures when excited in the UV region (see Label-Free bacterial imaging with Deep-UV-laser induced native fluorescence, Bhartia, Salas, Hug, Reid, A. Lane, Edwards, Nealson, 2010). Excitation Emission Matrix (EEM) has been proposed as a potential tool for water monitoring, but EEM only makes inferences (see Fluorescence as a potential monitoring tool for recycled water systems: A review, Henderson et al. 2009).

Real-World Example of Contaminated Tap Water

Figure 33:
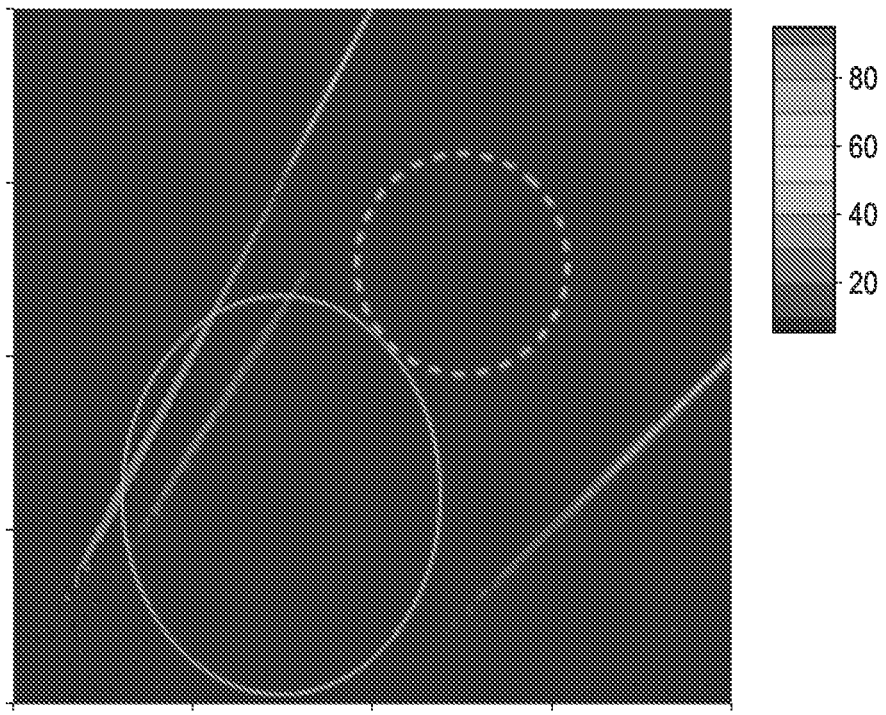
FIG. 33 shows fluorescence of clean, distilled water.
Figure 34:
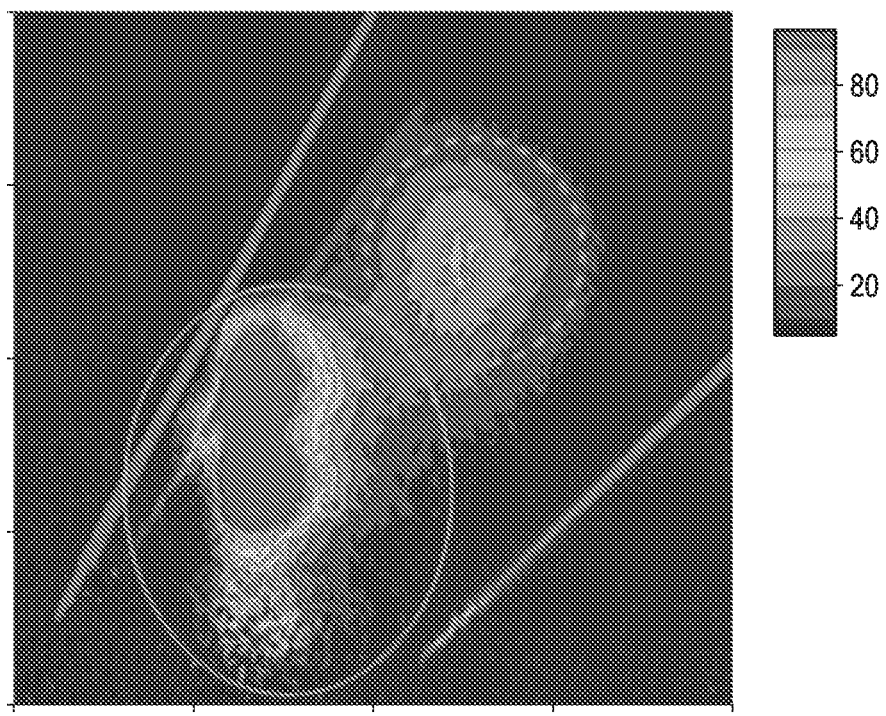
FIG. 34 shows fluorescence of contaminated restaurant water.

Pure water would show no fluorescence signature when doing an EEM. However, bacteria and various other contaminants fluoresce in the region marked by the blue circle. Some tap waters show a residual signature (green perforated circle) in a region that is linked to dissolved organic matter (DOM). This sample was taken from a restaurant in Marin County, CA USA. FIG. 33 shows clean, distilled water, while FIG. 34 shows contaminated restaurant water.

Discovered Unique Signatures Between Different Biologies

Figure 35:
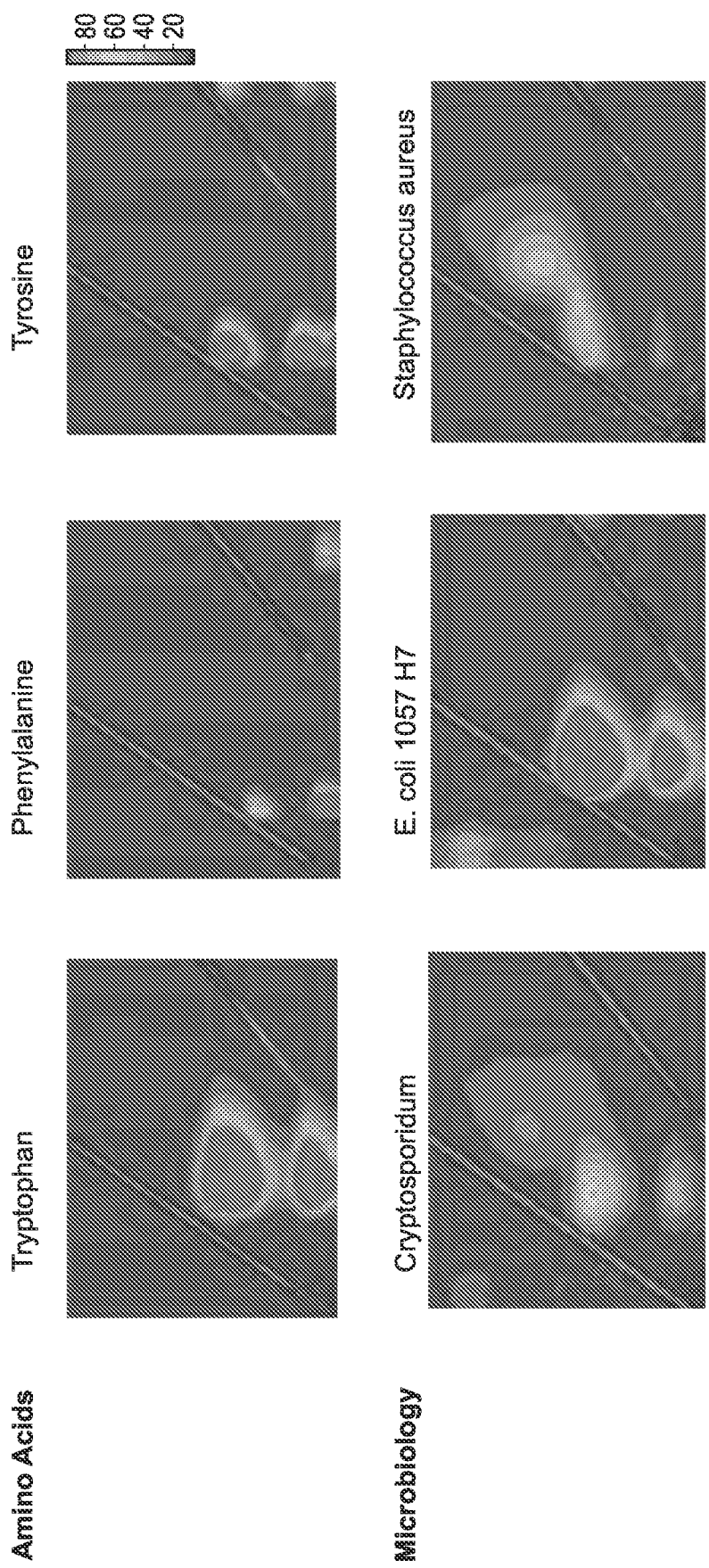
FIG. 35 shows fluorescence signatures of amino acids and microbiology.

Fluorescence profiles of the cells are due to the amino acids signatures. Not only is there a difference in amino acid composition for each strain, but they are most likely dynamically changing depending on life-cycle of the cell (alive>growing>dying>dead). FIG. 35 shows fluorescence signatures of amino acids and microbiology.

AI has Advanced Native-Induced Fluorescence Technology to Identify Microbiology

Figure 36:
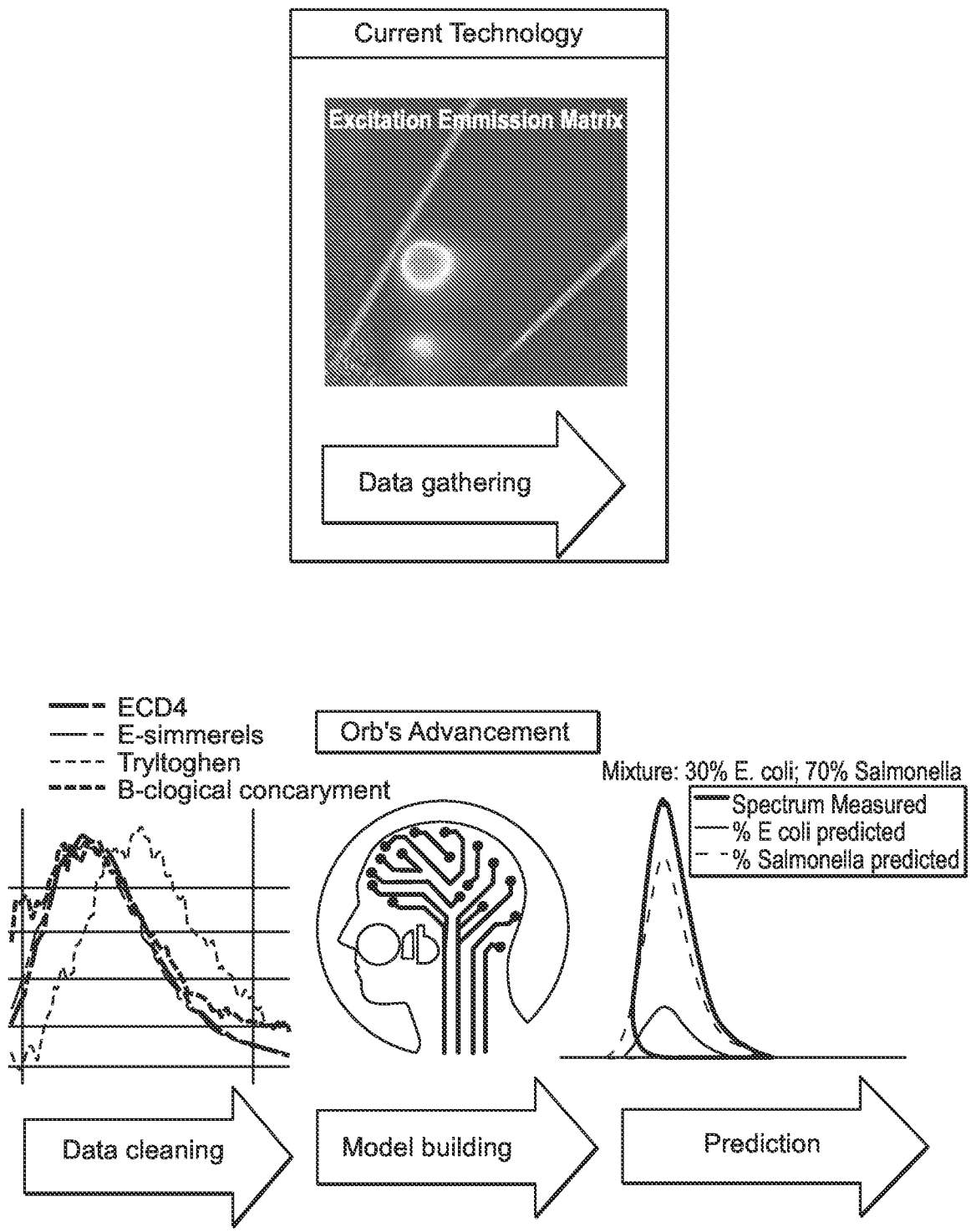
FIG. 36 compares current technology to advancements of the invention (Orb).

Fluorescence signatures from bacteria are mainly thought to be from tryptophan; however, we have found a stark difference between the signatures for *E. coli, Salmonella, Staphylococcus aureus, Listeria monocytogenes* and other dissolved organic matter (DOM). FIG. 36 compares current technology to advancements of the invention (Orb).

Ability to Quantify

Correlation data has been geared towards testing the invention's classification and quantification algorithm against known enumerated bacteria. To date, the invention has >98% accuracy when identifying bacteria (*E. coli, Salmonella, Staphylococcus aureus, Listeria*) in tap water that contained other fluorescing biological contaminants to challenge the system. FIG. 37 shows a concentration curve.

Figures 39, 40:
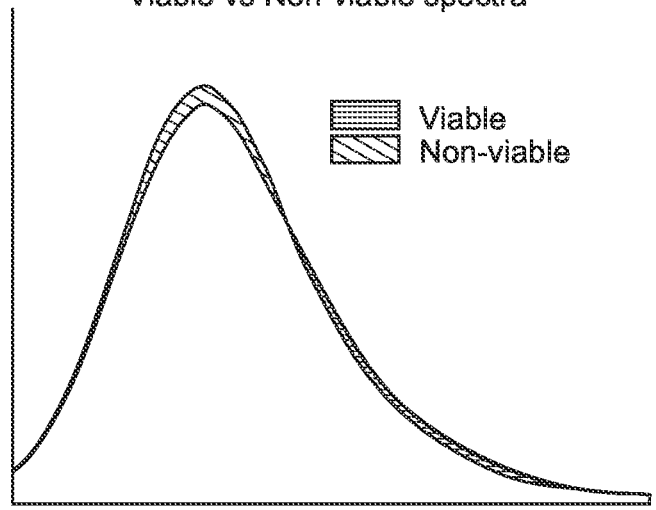
FIG. 39 shows a table of R2 predicted vs. actual composition.
FIG. 40 shows the spectral profile for *E. coli* when viable (live) and confirmed non-viable (dead) after autoclaving.

Deconvolution Study: Specifying Individual Bacteria from a Multi-Species Mixture With the invention's library of bacteria signatures, it is possible to break down individual bacterial species in a mixture and predict the presence and quantity of each. FIG. 38 shows deconvolution of a bacterial mixture. FIG. 39 shows a table of $R^2$ predicted vs. actual composition.

Deconvolution Study: Dead Vs Live Bacteria

Figures 41, 42:
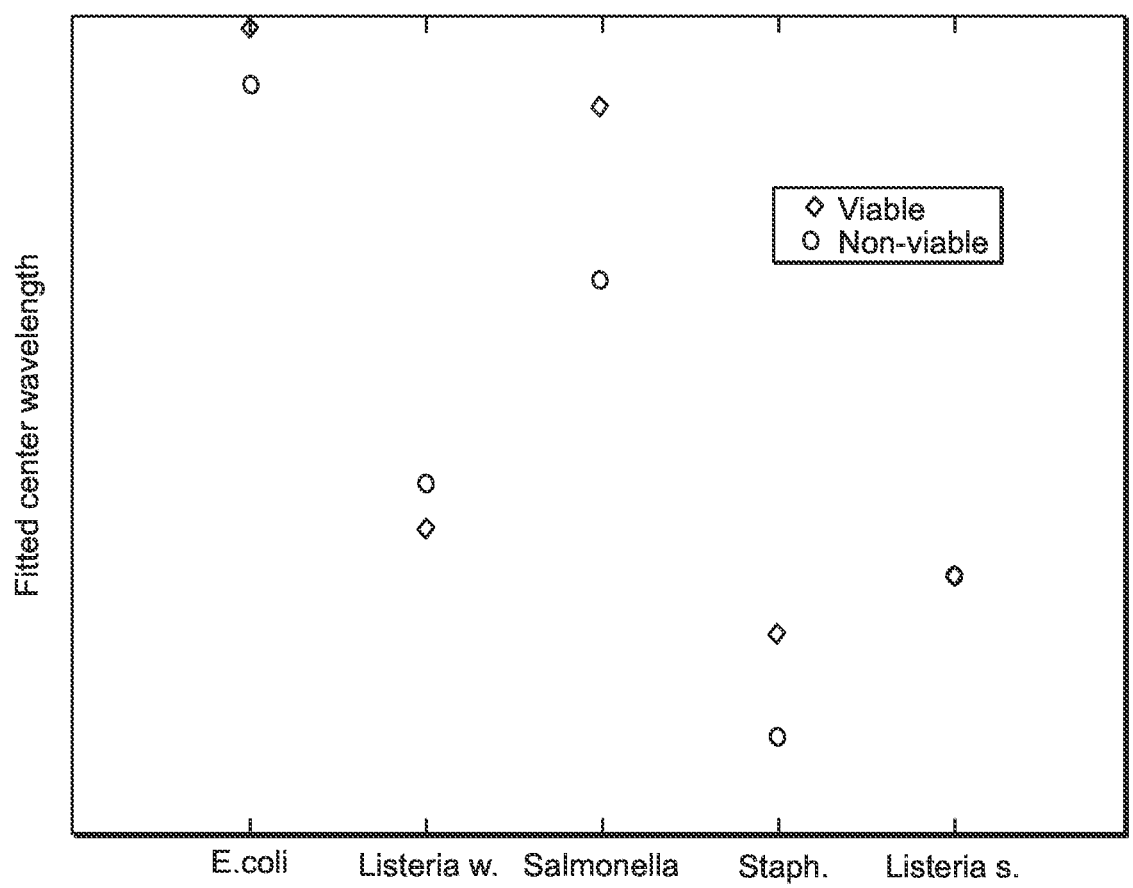
FIG. 41 shows the emission center wavelength for various bacterial species when viable (live) and confirmed non-viable (dead) after autoclaving.
FIG. 42 shows a table of R2 predicted vs actual viability.

The invention can accurately differentiate and determine the quantity of viable bacteria in a mixture of dead vs. live cells. FIG. 40 shows the spectral profile for *E. coli* when viable (live) and confirmed non-viable (dead) after autoclaving. FIG. 41 shows the emission center wavelength for various bacterial species when viable (live) and confirmed non-viable (dead) after autoclaving. FIG. 42 shows a table of $R^2$ predicted vs actual viability.

Cross Validation Study: Food Process Wash Water

Figure 43:
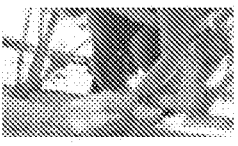
FIG. 43 shows different sources for detection using the invention (Orb) and the EPA approved method (coliform/*E. coli*).

An aim of the invention was to predict the presence/absence of *E. coli* from samples collected from various waters in one of North America's largest fresh produce processing plants. The invention's algorithm classified the samples in relation to the fluorescence database we have curated from measuring known pathogens in our facility. The highlighted region was the only discrepancy of the invention (Orb) detection vs EPA approved method for detection of *E. coli*. This could be due to the sample containing bacteria that were non-culturable. FIG. 43 shows different sources for detection using the invention (Orb) and the EPA approved method (coliform/*E. coli*).

Figure 44:
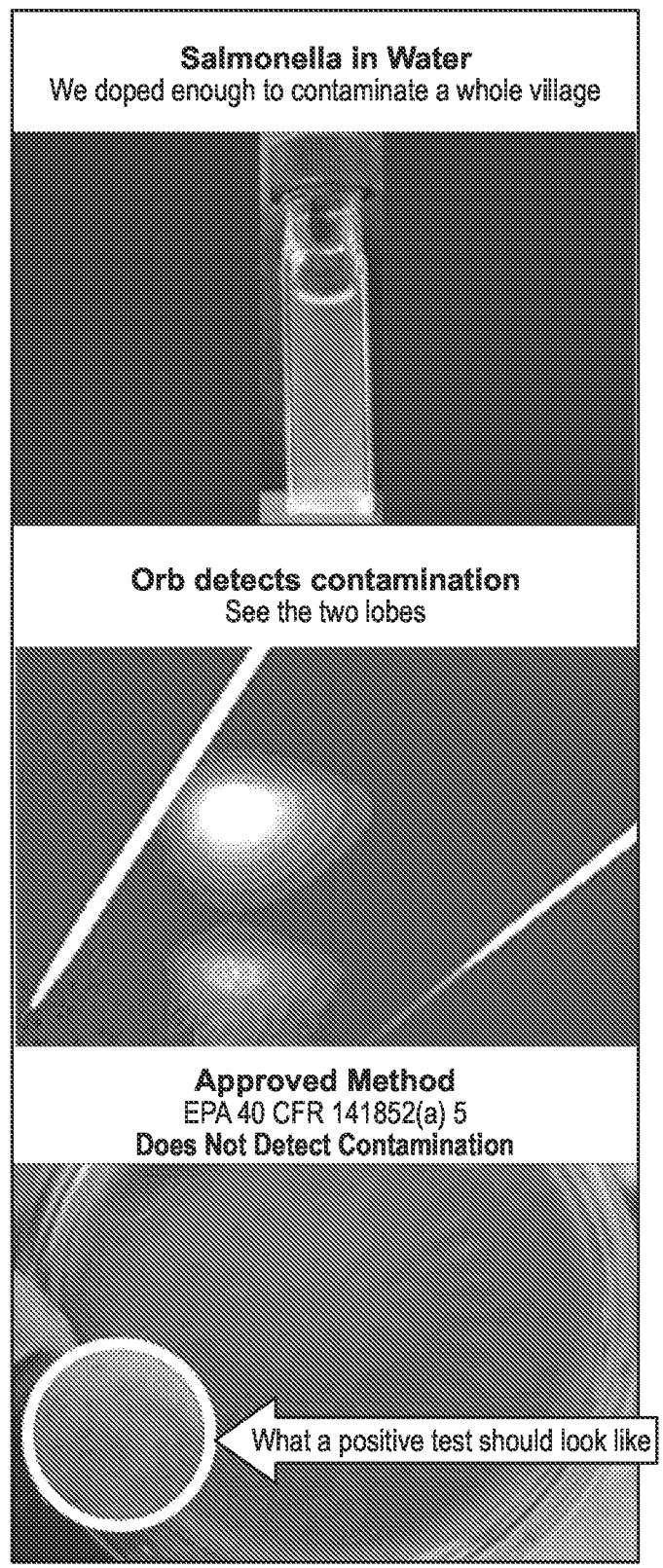
FIG. 44 shows an outline of a test method of the invention where a source was doped with *salmonella*, the invention was used to detect contamination, and the approved Gold Standard EPA method was used to detect contamination.

Total Microbial Load (TML) can be the Real-Time Monitoring Indicator of Water Safety Complimenting the Randomized Spot-Check *E. coli* or Coliform Test WHO and EPA waterborne disease initial screening methods do not detect non-coliform or protozoan pathogens such as: *Salmonella, Cryptosporidium, Giardia, Listeria* etc. Orb can detect all microbiology present in a given sample—even if we can't specify them—giving insights normally never detected and adding a complimentary layer of intelligence to current methods such as when to actually take a coliform test. The Gold Standard failed to detect pathogens after 24 hours, while the invention (Orb) detects in seconds, e.g. 3 seconds. FIG. 44 shows an outline of a test method of the invention where a source was doped with *salmonella*, the invention was used to detect contamination, and the approved Gold Standard EPA method was used to detect contamination. FIG. 45 shows results of the comparison of detection using the invention (Orb) to the Gold Standard detection.

Target Library Continually Grows

FIG. 46 shows a selection of detection capabilities to date. Moreover, the invention provides additional capabilities of surface scanning, food scanning, and bio-fluid scanning. In surface scanning, the invention is used to scan stainless steel and aluminum surfaces for pathogen monitoring and cleanliness proof statements. In food scanning, the invention is used to monitor food contamination from pathogens and select chemicals. In bio-fluid scanning, the invention is used to monitor urine for protein levels and infection.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for determining that a medium comprises a biological substance, the method comprising:
   directing one or more wavelengths of light that are each within a deep ultraviolet (UV) spectrum into a medium comprising a biological substance to thereby excite the biological substance in the medium;
   detecting emission from the excited biological substance via a plurality of semiconductor photodetectors, wherein each of the semiconductor photodetector detects only a subset of emission from the excited biological substance, thereby producing deep UV emission data;
   analyzing the deep UV emission data for presence of a deep UV spectral signature indicative of the biological substance, wherein presence of the deep UV spectral signature indicates that the medium comprises a biological substance; and
   at least two of the plurality of semiconductor photodetectors overlap in the subset of emission from the excited biological substance that each detects.

2. The method of claim 1, wherein the emission is in a detection range of 300-400 nm.

3. The method of claim 1, wherein at least six semiconductor photodetectors are employed in the detecting step.

4. The method of claim 1, wherein the plurality of semiconductor photodetectors are avalanche photodiode detectors or silicon sensors.

5. The method of claim 1, wherein the medium is selected from the group consisting of a biofluid, water, an aluminum surface, a stainless steel surface, and a metallic surface.

6. The method of claim 1, wherein the biological substance is a pathogen.

7. The method of claim 6, wherein the biological substance is a pathogen and the medium is water.

8. The method of claim 1, wherein the method is performed in a state similar to Earth's atmospheric conditions.

9. The method of claim 1, wherein the method is performed outside of the Earth's atmospheric conditions.

10. A system for determining that a medium comprises a biological substance, the system comprising:
    one or more excitation sources, each operating in a deep ultraviolet (UV) range for excitation of a biological substance in a medium;
    a detector comprising a plurality of semiconductor photodetectors;
    wherein the system is configured such that each semiconductor photodetector detects only a subset of emission from the excited biological substances; and
    at least two of the plurality of semiconductor photodetectors overlap in the subset of emission from the excited biological substance that each detects.

11. The system of claim 10, wherein the emission is in a detection range of 300-400 nm.

12. The system of claim 10, wherein the system comprises at least six semiconductor photodetectors.

13. The system of claim 10, further comprising a processor configured to process data received from the plurality of semiconductor photodetectors.

14. The system of claim 13, wherein the processor is integrated into the system.

15. The system of claim 13, wherein the processor is remote from the system.

16. The system of claim 13, wherein the processor is a computer, smart phone, or microcontroller.

17. The system of claim 10, wherein the system is a portable, handheld, point-and-shoot system.

18. The system of claim 10, wherein the biological substance is a pathogen and the system is configured such that each semiconductor photodetector detects only a subset of emission from the excited pathogen to produce a deep UV spectral signature indicative of presence of the pathogen in the medium.

\* \* \* \* \*